(12) United States Patent
Balaban

(10) Patent No.: US 7,067,135 B2
(45) Date of Patent: Jun. 27, 2006

(54) **METHODS AND COMPOSITIONS FOR THE TREATMENT AND PREVENTION OF *STAPHYLOCOCCUS AUREUS* INFECTIONS**

(76) Inventor: Naomi Balaban, 813 Lake Terrace Cir., Davis, CA (US) 95616

( * ) Notice: Subject to any disclaimer, the term of this patent is extended or adjusted under 35 U.S.C. 154(b) by 423 days.

(21) Appl. No.: 09/839,695

(22) Filed: Apr. 19, 2001

(65) Prior Publication Data

US 2004/0077534 A1    Apr. 22, 2004

Related U.S. Application Data

(63) Continuation-in-part of application No. 09/054,331, filed on Apr. 2, 1998, now Pat. No. 6,291,431.

(60) Provisional application No. 60/068,094, filed on Dec. 19, 1997.

(51) Int. Cl.
- A61K 39/02 (2006.01)
- A61K 39/00 (2006.01)
- A61K 39/40 (2006.01)
- A61K 39/38 (2006.01)
- A61B 5/055 (2006.01)

(52) U.S. Cl. .............. 424/190.1; 424/9.34; 424/91.51; 424/93.42; 424/165.1; 424/184.1; 424/185.1; 424/190.1; 514/44; 530/388.2; 530/388.21; 536/23.7

(58) Field of Classification Search ................ 424/9.2, 424/130.1, 150.1, 184.1, 185.1, 190.1, 234.1, 424/278.1, 282.1, 9.34, 91.51, 93.42, 165.1; 930/10, 200; 514/44; 530/388.2, 388.21; 536/23.7
See application file for complete search history.

(56) References Cited

FOREIGN PATENT DOCUMENTS

| EP | 0 395 099 A | 10/1990 |
|---|---|---|
| WO | WO96/10579 | 4/1996 |
| WO | WO 96 10579 A | 4/1996 |
| WO | WO97/44349 | 11/1997 |
| WO | WO 97 44349 A | 11/1997 |
| WO | WO 99/32133 * | 7/1999 |
| WO | WO 99 32133 A | 7/1999 |

OTHER PUBLICATIONS

Balaban et al. 1998. Science. vol. 280 : 438-440.*
Balaban et al. 1995. PNAS. vol. 92:1619-1623.*
Lee.1998. Trends in Micrbiol. vol. 6(12):461-463.*
Balaban et al., "Autocrine regulation of toxin synthesis by *Staphylococcus aureas*" Proc.Natl. Acad. Sci. USA (1995) 92:1619-1623.

(Continued)

Primary Examiner—Lynette R. F. Smith
Assistant Examiner—J. Hines
(74) Attorney, Agent, or Firm—Jeffrey Weiss; Janine Rickman Novatt; Weiss, Moy & Harris, P.C.

(57) ABSTRACT

The invention features methods and compositions for treatment or prevention of infection by, or disease caused by infection with, *Staphylococcus* spp., particularly *S. aureus*.

2 Claims, 12 Drawing Sheets

OTHER PUBLICATIONS

Balaban et al., "Translation of RNAIII, the *Staphylococcus aureas agr* regulatory RNA molecule, can be activated by a 3'-end deletion" *FEMS Microbiol. Letters* (1995) 133:155-161.

Balaban et al., "Autoinducer of Virulence As a Target for Vaccine and Therapy Against *Staphylococcus aereus*" *Science* (1998) 280:438-440.

Ji, et al. "Cell Density Control of Staphylococcus Virulence Mediated by an Octapeptide Pheromone," *Proc. Natl. Acad. Sci. USA* (1995) 92:12055-12059.

Mayville, et al. "Structure-Activity Analysis of Synthetic Autoinducing Thiolactone Peptides form *Staphylococcus aureus* Responsible for Virulence," *Proc. Natl. Acad. Sci. USA* (1999) 96:1218-1223.

* cited by examiner

Fig. 1B,C
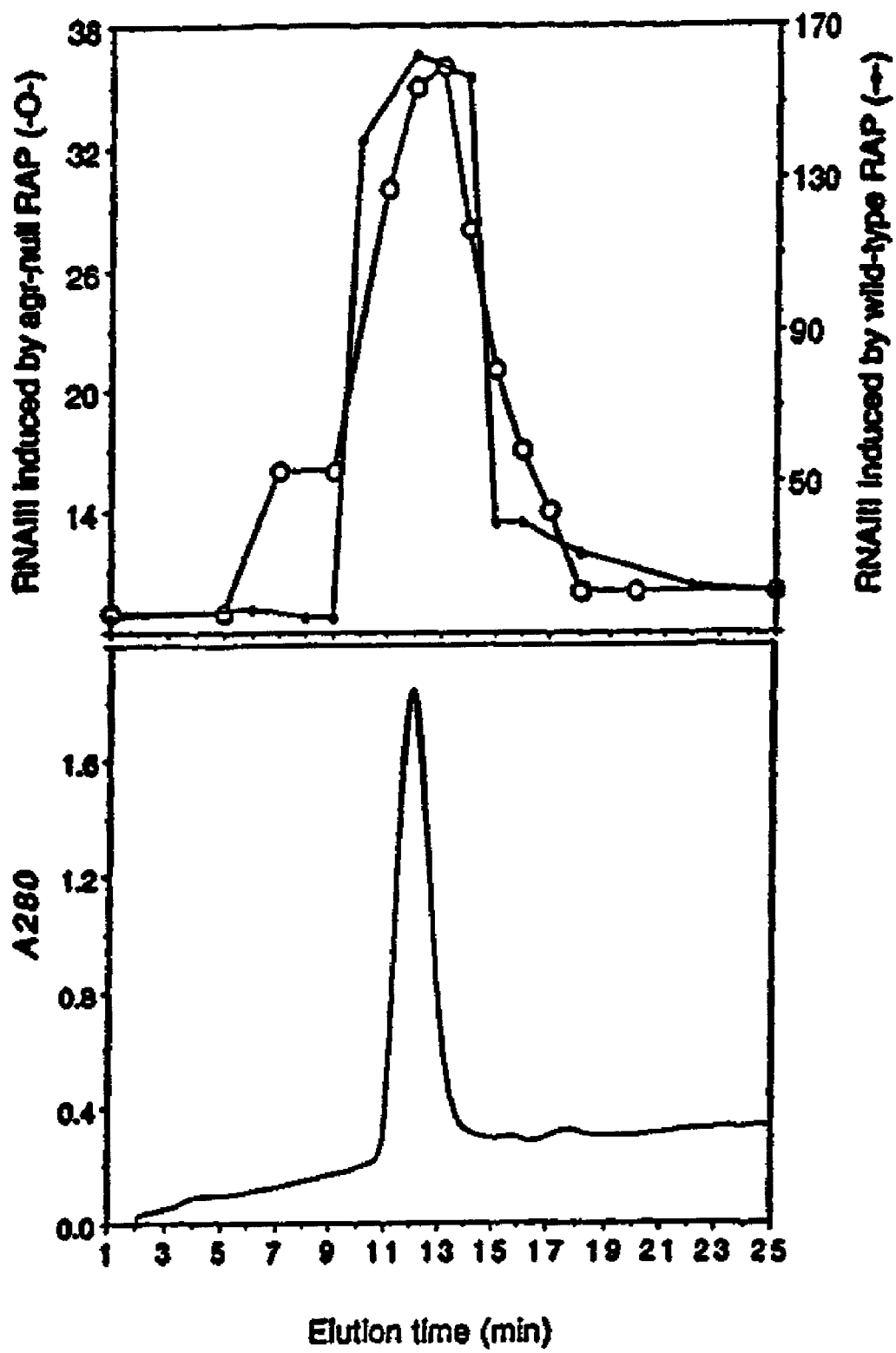

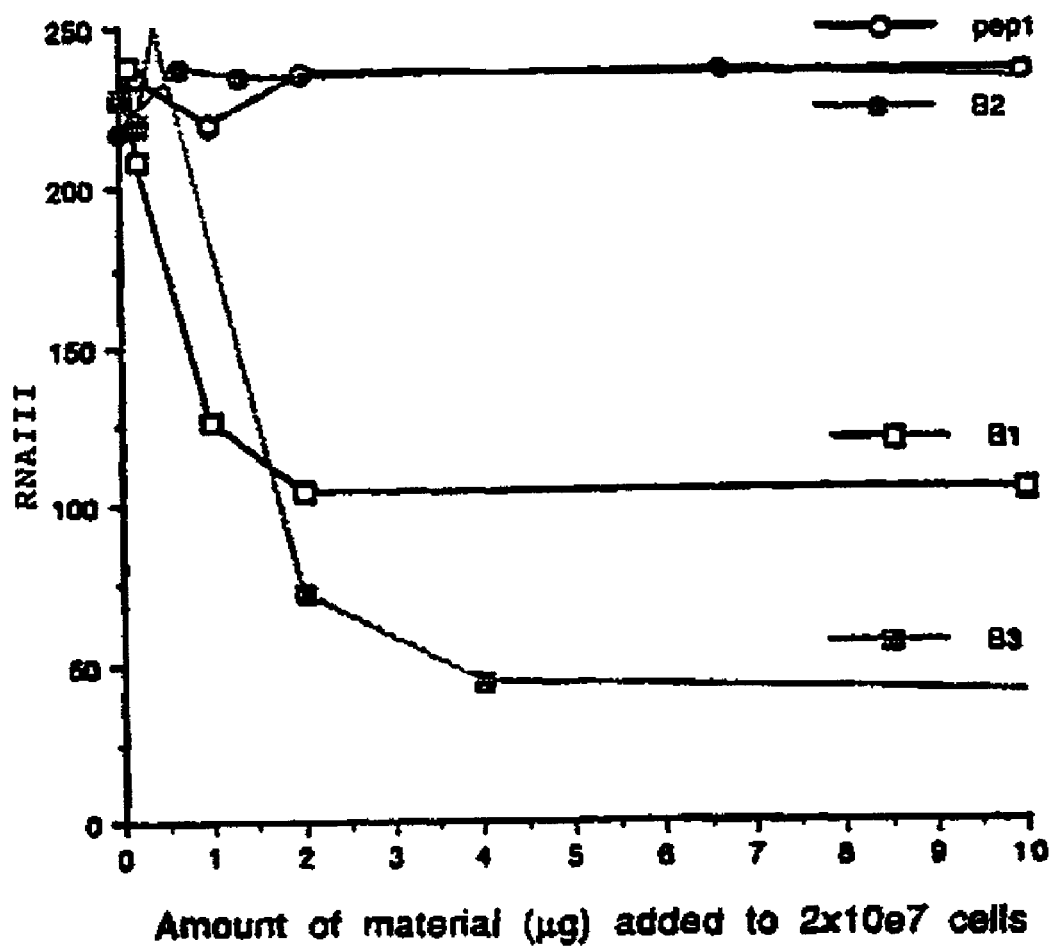

```
ATGGCTATTAAAAAGTATAAGCCAATAACAAATGGTCGTCGTAATATGACTTCGTTAGATTTCGCAGAAATCACGAAAACTACACCTGAAAAGTCATTATTA  102
 M  A  I  K  K  Y  K  P  I  T  N  G  R  R  N  M  T  S  L  D  F  A  E  I  T  K  T  T  P  E  K  S  L  L
AACCGCTACCGAAAAAGCGGGACGTAACAACCAAGGTAAATTGACTGTAAGACACCATGGTGGACACAAACGTCAATACCGTGTTATCGATTTCAAA        204
 K  P  L  P  K  K  A  G  R  N  N  Q  G  K  L  T  V  R  H  H  G  G  H  K  R  Q  Y  R  V  I  D  F  K
CGTAACAAAGATGGTATCAATGCAAAAGTTGATTCTATTCAATATGATCCAAACCGCTCAGCAAACATCGCTTTAGTTGTATATGCAGACGGTGAAAAACGA  306
 R  N  K  D  G  I  N  A  K  V  D  S  I  Q  Y  D  P  N  R  S  A  N  I  A  L  V  V  Y  A  D  G  E  K  R
ATATATCATTGCATTGCTCCTAAAGGATTAGAAGTAGGTCAAATCGTTGAAAGTGGTGCTGAAGCTGACACTAAAGTTGGTAACGCATTACCATTACAAAAC  408
 I  Y  H  C  I  A  P  K  G  L  E  V  G  Q  I  V  E  S  G  A  E  A  D  T  K  V  G  N  A  L  P  L  Q  N
ATTCCAGTTGGTACAGTAGTACACAACATCGAGCTTAAACCTGGTAAAGGTGGACAAATCGCTCGTTCAGCTGGTGCAAGTGCTCAAGTACTTGGTAAAGAA  510
 I  P  V  G  T  V  V  H  N  I  E  L  K  P  G  K  G  G  Q  I  A  R  S  A  G  A  S  A  Q  V  L  G  K  E
GGTAAATACGTTATTAATCAGATTAAGATCTGTGAAGTTCGTATGATTCTTATCTTGCCGTGCTACAATCGGTCAAGTTGGTAACCTACAACACGAATTA    612
 G  K  Y  V  L  I  R  L  R  S  G  E  V  R  M  I  L  S  T  C  R  A  T  I  G  Q  V  G  N  L  Q  H  E  L
GTTAACGTTGGTAAAGCCGGACGTTCAAGATGGAAAGGTATCCGTCCAACAGTTCGTGGTTCTGTAATGAACCCTCACCCACACGGTGGTGGTGAA        714
 G  K  Y  V  L  I  R  S  G  E  V  R  W  K  G  I  R  P  T  V  R  G  S  V  M  N  P  N  D  H  P  H  G  G  E
GTTAACGTTGGTAAAGCCGGTAGCCGTGTCAAGTCACCATGGGGTAACCATGGCTTGGTAAGAAAATCATCAGACAAACTTATC                     816
 V  N  G  K  A  G  R  S  R  W  K  G  I  R  P  T  V  R  G  S  V  M  N  P  N  D  H  P  H  G  G  E
GGTCGTGCTCCTATCGGTAGACCATCTCCAATGTCACCATGGGGTAACCATGGCTTGGTAAGAAAATCATCAGACAAACTTATC
 G  R  A  P  I  G  R  P  S  P  M  S  P  W  G  K  P  T  L  G  K  K  T  R  R  G  K  K  S  S  D  K  L  I
GTTCGTGGACGTAAGAAAAAATAA
 V  R  G  R  K  K  K  *
```

Fig. 5. DNA and Amino Acid sequence of RAP.

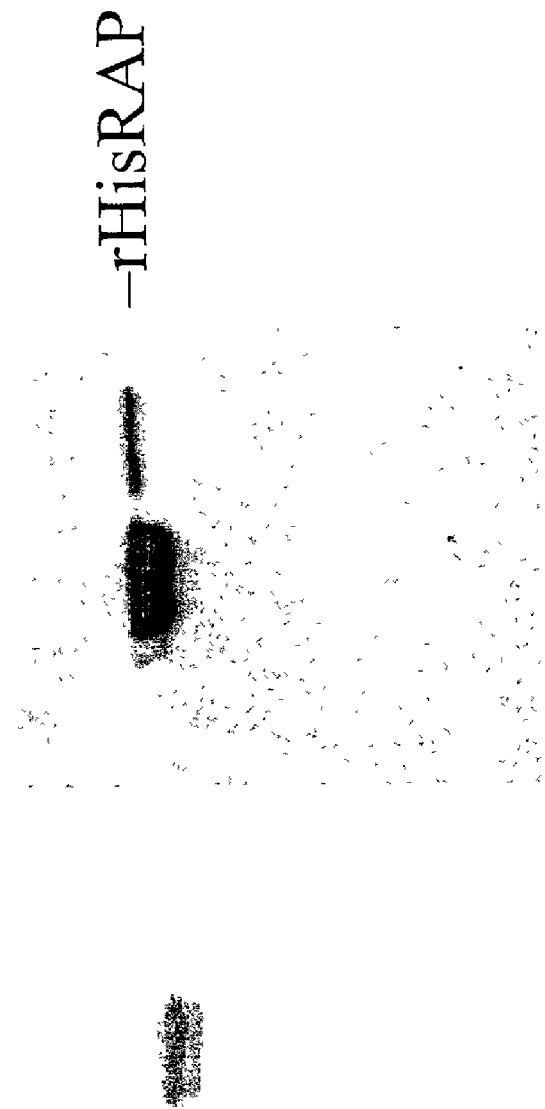

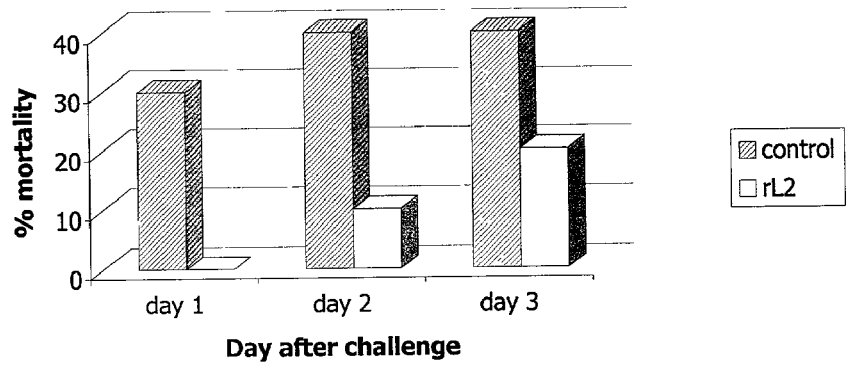
Fig. 7: Vaccination of Balb/c mice with rL2 and challenge with 2x10e9 *S. aureus* SD
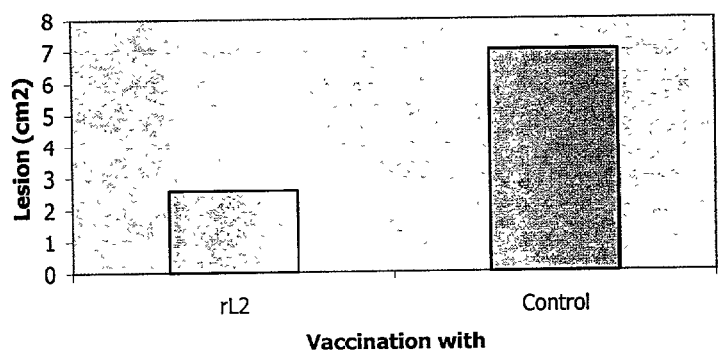
Fig. 8: Development of lesion in rL2 vaccinated animals that survived a challenge of 2x10e9 *S. aureus* cells

METHODS AND COMPOSITIONS FOR THE TREATMENT AND PREVENTION OF *STAPHYLOCOCCUS AUREUS* INFECTIONS

CROSS-REFERENCE TO RELATED APPLICATIONS

This application is a continuation-in-part of U.S. application Ser. No. 09/054,331, filed Apr. 2, 1998 now U.S. Pat. No. 6,291,431, which application claims the benefit of U.S. provisional application Ser. No. 60/068,094, filed Dec. 19, 1997, now abandoned, each of which applications is incorporated by reference in its entirety herein for all purposes.

TECHNICAL FIELD

The present invention relates to methods and compositions for treatment or prevention of bacterial infection, diseases or symptoms caused by bacterial infection, and particularly those associated with infection by *Staphylococcus* spp.

BACKGROUND OF THE INVENTION

*Staphylococcus aureus* causes disease chiefly through the production of virulence factors such as hemolysins, enterotoxins and toxic shock syndrome toxin. The synthesis of virulence factors in *S. aureus* is controlled by a regulatory RNA molecule, RNAHI (Novick, etal., *EMBO J.* 12, 3967 (1993), Balaban et al., *FEMS Microbiol Letts.* 133, 155 (1995), Moerfeldt et al., *EMBO J.* 14, 4569 (1995)), encoded by the agr locus. The rnaiii gene of the agr locus is transcribed in culture only from the midexponential phase of growth, and is autoinduced by the protein RNAIII activating protein (RAP) (Balaban et al., *Proc. Natl. Acad. Sci. USA*. 92,1619 (1995)). RAP is continuously secreted by the bacteria and only activates RNAIII at a concentration threshold (ibid).

The growth-phase associated regulation of *S. aureus* virulence factor synthesis is controlled by a quorom sensing mechanism. The control of virulence factor production is a complex process, which apparently involves multiple global regulatory loci. One of these regulatory loci, the agr locus, contains two divergent transcription units, RNAII and RNAIII, both of which are active only from the midexponential phase of growth and are autocatalytic (Novick et al. *Mol. Gen. Genet.* 248:446058 (1995)). RNAIII, an RNA regulatory molecule encoded by the agr locus, upregulates genes encoding for toxic exomolecules while down regulating genes encoding for surface molecules, resulting in vivo in dissemination and disease (Novick et al. *EMBO J.* 12:3967–75 (1993); Balaban et al. *Proc. Natl. Acad. Sci. USA* 92:1619–23 (1995); Moerfeldt et al. *EMBO J.* 14:4569–77 (1995)). The RNAII locus regulates the expression of RNAIII. The RNAII locus comprises four open reading frames (ORFs), agrA, agrB, agrC, and agrD. The agrA and agrC genes encode for a classical two-component signal transduction pathway, with agrC encoding a signal receptor and agrA the response regulator.

The autoinducers of RNAIII that have been described to date include the agr-independent RNAIII activating protein (RAP) (Balaban et al (1995) supra), and the agrD-derived octapeptide pheromone (Ji et al. *Proc. Natl. Acad. Sci.* 92:12055–9 (1995)). The agrD-derived octapeptide has also been shown to be part of a "bacterial interference" system that provides a mechanism for different *S. aureus* strains to compete with each other at an infection site (Ji et al. *Science* 276:2027–30 (1997)). In this bacterial interference system, the octapeptide activates RNAIII transcription of the strain by which it is produced, while also acting as an inhibitor of RNAIII transcription of other strains of *Staphyloccocus*.

In addition to agr, the sar locus also plays a role in regulation of *S. aureus* virulence factor production. The sar locus comprises a sarA ORF preceded by a triple promoter region interspersed with two putative smaller ORFs (ORF3 and ORF4). The triple promoter system yields three overlapping sar transcripts (sarA, sarC and sarB) (Bayer et al. *J. Bacteriol.* 178:4563–70 (1996)).

In vivo *S. aureus* first produce proteins that facilitate bacterial binding to host cells as well as the secreted autoinducer molecules. As the bacterial colony increases in density, the autoinducer molecules accumulate. Upon reaching a threshold concentration, the autoinducers activate RNAIII transcription, which in turn results in virulence factor production. The virulence factors damage and eventually destroy surrounding host cells, which serve as nutritive sources for the *S. aureus* bacteria and promoting further growth of the colony. Thus, inhibition of RNAIII by suppression of the autoinducers or their receptors is of particular interest in treatment or prevention of *S. aureus*-mediated disease. Several mechanisms for RNAIII inhibition have been identified, including inhibition of RNAIII by anti-RAP antibodies and by a peptide termed the RNAIII inhibiting peptide (RIP), which competes with RAP (Balaban et al. (1995) supra).

*S. aureus* causes diseases ranging from minor skin infections to life-threatening deep infections such as pneumonia, endocarditis, meningitis, post-operative wound infections, septicemia, and toxic shock syndrome (Silverstein et al., in *Microbiology,* Davis et al., eds. (Lippincott, Philadelphia, 1990), pp. 485–506). Hospitalized patients are at particular risk, with over 500,000 nosocomial infections per year (Panlilio, et al., *Inf. Contr.and Hasp. Epidem.* 13, 582 (1992)). The emergence of drug resistance has made many of the available antimicrobial agents ineffective. Therefore, alternative methods for the prevention and treatment of bacterial infections in general and *S. aureus* infections in particular are eagerly sought. The instant invention addresses this need and others.

SUMMARY OF THE INVENTION

The invention features methods and compositions for treatment or prevention of infection by, or disease caused by infection with, *Staphylococcus* spp., particularly *S. aureus*.

One aspect of the invention is a composition comprising a polypeptide comprising an amino acid sequence comprising the general formula Y(K or S) PXTNF (SEQ ID NOS:1 and 2), where X is C, W, or I. Pharmaceutical compositions are also provided in some embodiments. A further aspect of the invention is a composition of claim 1, wherein the polypeptide comprises an amino acid sequence comprising the general formula IKKY(K or S)PXTNF (SEQ ID NOS:3 and 4), where X is C, W, or I.

A further aspect of the invention is a method for treating a host for a staphylococcal infection, wherein the composition of claim 1 is administered to the host. In some embodiments the host is a human patient. In further embodiments the host is an animal, such as but not limited to an experimental animal.

A further aspect of the invention is a method for treating a host for a staphylococcal infection, wherein an antagonist of the RAP receptor is administered to the host. In some embodiments the host is a human patient. In further embodiments the host is an animal, such as but not limited to an experimental animal. In some embodiments the antagonist is a polypeptide, a peptidomimetic, or an antibody.

A further aspect of the invention is a nucleic acid molecule encoding a polypeptide of the invention. The nucleic acid molecule can be RNA or DNA or an antisense nucleic acid molecule. In an embodiment, the nucleic acid molecule comprises the nucleotide sequence TAT TCG CCG TGG ACC AAT TTT (SEQ ID NO:5).

In another aspect, the invention features an isolated RAP polypeptide, as well as nucleic acid encoding such RAP polypeptides.

BRIEF DESCRIPTION OF THE FIGURES

FIG. 1B is a graph depicting the ability of 1 ml fractions collected from postexponential supernatants of wild type S. aureus and of arg-null S. aureus fractionated on a gel filtration to activate RNAIII.

FIG. 1C is a graph depicting the absorbance at $A_{280}$ of fractions from FIG. 1B containing peak RNAIII-inducing activity.

FIGS. 4A and 4B are graphs depicting the inhibition of RNAIII by synthetic RIP peptides.

FIG. 5 is a schematic illustrating the DNA (SEQ ID NO: 12) and amino acid (SEQ ID NO: 13) sequences of RAP.

FIGS. 6A and 6B are photograph of gels showing purification of recombinant RAP (rRAP) eluted from a nickel column by 1M (lane 1), 2M (lane 2) and 3M (lane 3) imidazole applied to SDS 12.5% PAGE. The gel was Western blotted, membrane stained in ponceau to visualize proteins (FIG. 6A), blocked in milk, and incubated with anti-histidine antibodies (FIG. 6B). Bound antibodies were detected by peroxidase-conjugated anti-mouse antibodies, and visualized by ECL (Amersham). Molecular mass is indicated in kDa.

FIG. 7 is a graph showing the percent mortality of Balb/c naive mice (control) or mice vaccinated with rL2, and challenged with $2 \times 10^9$ S. aureus.

FIG. 8 is a graph showing the development of lesions in rL2 vaccinated animals that survived a challenge of $2 \times 10^9$ S. aureus.

DETAILED DESCRIPTION OF THE INVENTION

Figure 1A:
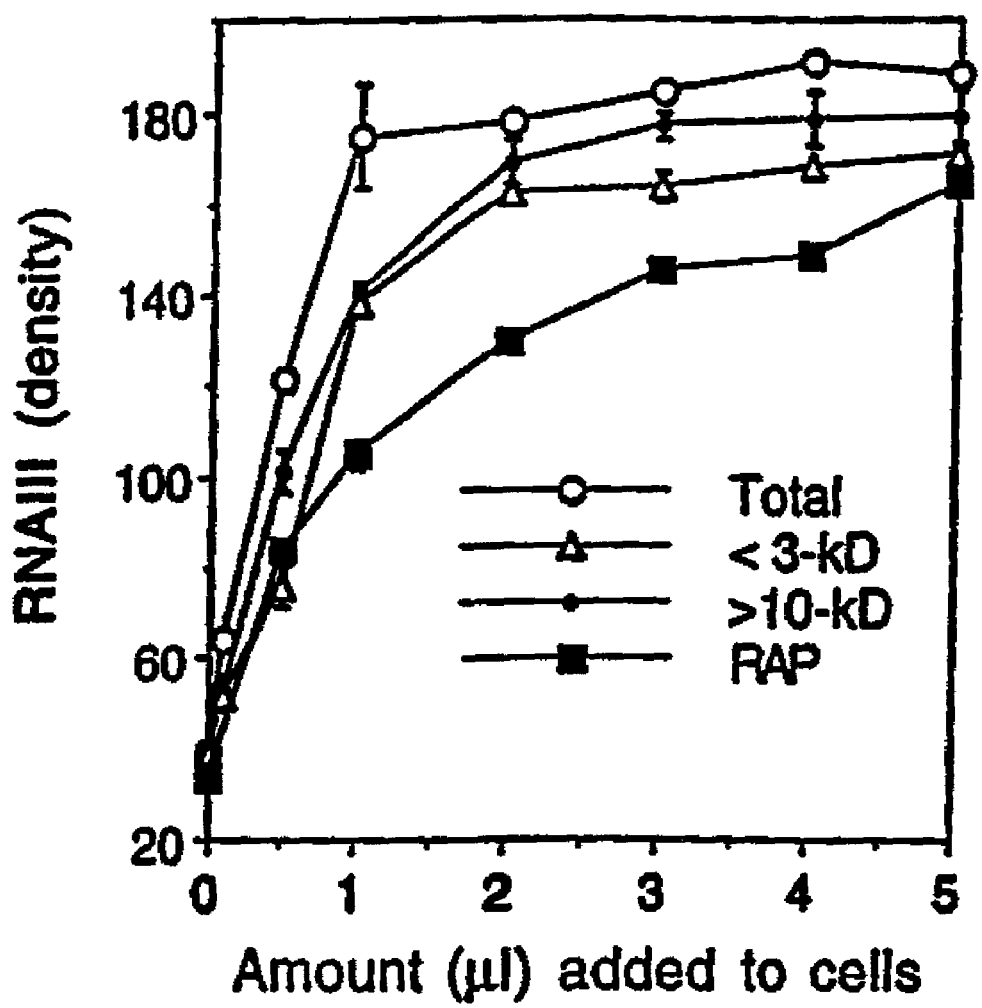
FIG. 1A is a graph depicting an assay for RNAIII activation as described in Balaban et al. (supra). Post-exponential supernatants of wild-type S. aureus (denoted total) were filtered through a 3-kD cutoff membrane and the flow-through containing agrD-encoded octapeptide (Guangyong, et al, Proc. Natl. Acad. Sci. U.S.A. 92, 12055 (1995)) collected (denoted <3-kD). Retained material (containing RAP) was filtered through a 10-kD cutoff membrane. Material greater than 10-kD (denoted >10-kD) was applied to an HPLC gel filtration column and purified RAP was collected (RAP). Increasing amounts of each of these compositions were added to early exponential wild type S. aureus and tested for their ability to activate RNAIII.
Figure 1D:
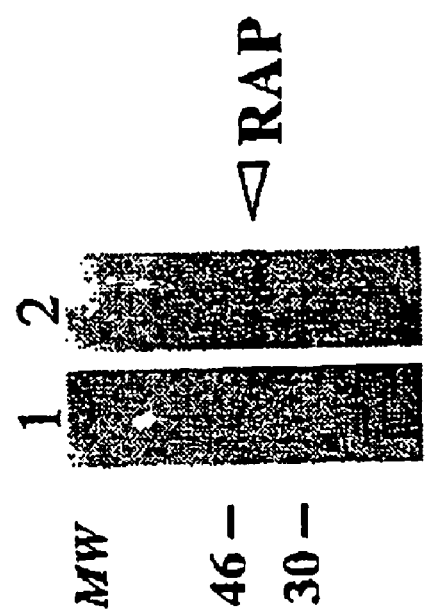
FIG. 1D is a photograph of gel-filtration-purified RAP from wild type (lane 1) and from agr-null strain (lane 2) separated on SDS PAGE and silver stained. Approximate molecular weight markers are indicated.

Before the present proteins, formulations and methods are described, it is to be understood that this invention is not limited to the particular compounds, characteristics and steps described, as such may, of course, vary. It is also to be understood that the terminology used herein is for the purpose of describing particular embodiments only, and is not intended to limit the scope of the present invention which will be limited only by the appended claims.

All publications and patents mentioned herein are incorporated herein by reference to disclose and describe the specific methods and/or materials in connection with which the publications and patents are cited. The publications and patents discussed herein are provided solely for their disclosure prior to the filing date of the present application. Nothing herein is to be construed as an admission that the present invention is not entitled to antedate such publication or patent by virtue of prior invention. Further, the dates of publication or issuance provided may be different from the actual dates which may need to be independently confirmed.

Generally, the nomenclature used hereafter, and the laboratory procedures in cell culture and protein biochemistry are those well known and commonly employed in the art. Generally, enzymatic reactions and column chromatography are performed according the manufacturer's specifications. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For the purposes of the present invention, the foregoing terms are defined below. The terms "pharmaceutically acceptable" or "therapeutically acceptable" refer to a substance which does not interfere with the effectiveness or the biological activity of the active ingredients and which is not toxic to the host or the patient.

The terms "encoding" or "encodes" refer generally to the sequence information being present in a translatable form, usually operably linked to a promoter. A sequence is operably linked to a promoter when the functional promoter enhances transcription or expression of that sequence. An anti-sense strand is considered to also encode the sequence, since the same informational content is present in a readily accessible form, especially when linked to a sequence which promotes expression of the sense strand. The information is convertible using the standard, or a modified, genetic code. See, e.g. Watson et a/., (1987) The Molecular Biology of the Gene. (4th Edition), Vols. 1 & 2, Benjamin, Menlo Park, Calif.

As used to refer to nucleic acid sequences, the term "homologous" indicates that two or more nucleotide sequences share a majority of their sequence. Generally, this will be at least about 70% of their sequence and preferably at least 95% of their sequence.

Another indication that sequences are substantially identical is if they hybridize to the same nucleotide sequence under stringent conditions (see, e.g., Sambrook etal., *Molecular Cloning—A Laboratory Manual,* Cold Spring Harbor Laboratory, Cold Spring Harbor, N.Y., 1985). Stringent conditions are sequence-dependent and will be different in different circumstances. Generally, stringent conditions are selected to be about 5° C. lower than the thermal melting point (T̂ for the specific sequence at a defined ionic strength and pH. The $T_m$ is the temperature (under defined ionic strength and pH) at which 50% of the target sequence hybridizes to a perfectly matched probe. Typically, stringent conditions will be those in which the salt concentration is at least about 0.2 molar at pH 7 and the temperature is at least about 60° C.

As used to refer to proteins, polypeptides, or peptides, which terms are used interchangeably here, the term "homologous" is meant to indicate two proteins or polypeptides'share a majority of their amino acid sequences. Generally, this will be at least 90% and usually more than about 95%. Homology for polypeptides or proteins is typically measured using sequence analysis software, see e.g. Sequence Analysis Software Package of the Genetics Computer Group, University of Wisconsin Biotechnology Center, 1710 University Avenue, Madison Wis. 53705. Protein analysis software matches similar sequences using measure of homology assigned to various substitutions, deletions, and other modifications. Conservative substitutions typically include substitutions within the following groups glycine, alanine; valine, isoleucine, leucine; aspartic acid, glutamic acid; asparagine, glutamine; senne, threonine; lysine, arginine; and phenylalanine, tyrosine.

As used herein the term "isolated" is meant to describe a compound of interest (e.g., either a polynucleotide or a polypeptide) that is in an environment different from that in which the compound naturally occurs. "Isolated" is meant to include compounds that are within samples that are substantially enriched for the compound of interest and/or in which the compound of interest is partially or substantially purified.

The term "isolated" as applied to, for example, nucleic acids, means a nucleic acid substantially separated from other macromolecules, cellular components, or DNA sequences which naturally accompany a native nucleic acid, e.g. ribosomes, polymerases, other nucleic acid sequences, and the like. The term includes a nucleic acid or polypeptide that has been removed from its naturally occurring environment, and includes recombinant or cloned DNA isolates and chemically synthesized analogues, and analogues biologically synthesized by heterologous systems. A substantially pure or biologically pure nucleic acid includes isolated forms of the nucleic acid.

The phrase "biologically pure" or "substantially pure" refers to material that is substantially or essentially free from components which normally accompany it as found in its native state, e.g., at least 60% free, preferably 75% free, and most preferably 90% free from other components with which it is naturally associated.

The term "recombinant" refers to a nucleic acid sequence which is not naturally occurring, or is made by the artificial combination of two otherwise separated segments of sequence, i.e. by chemical synthesis, genetic engineering, and the like.

The term "treatment" or "treating" means any therapeutic intervention in a mammal, preferably a human or bovine, including:

(i) prevention, that is, causing the clinical symptoms not to develop, e.g., preventing infection from occurring and/or developing to a harmful state;

(ii) inhibition, that is, arresting the development of clinical symptoms, e.g., stopping an ongoing infection so that the infection is eliminated completely or to the degree that it is no longer harmful; and/or (iii) relief, that is, causing the regression of clinical symptoms, e.g., causing a relief of fever and/or inflammation caused by an infection.

Treatment is generally applied to any mammal susceptible to of having an *S. aureus* infection (e.g., mammals, birds, etc.), generally a mammal, usually a human or bovine where the treatment can be applied for prevention of bacterial infection of for amelioration of active bacterial infection, where the bacteria is a *Staphylococcus* bacteria, specifically *Staphylococcus aureus*.

The terms "effective amount" and/or "therapeutic amount" means a dosage sufficient to provide treatment for the disease state being treated. This will vary depending on the patient, the disease and the treatment being effected. In the case of a bacterial infection, an "effective amount" is that amount necessary to substantially improve the likelihood of treating the infection, in particular that amount which improves the likelihood of successfully preventing infection or eliminating infection when it has occurred.

The term "protein" as used herein is intended to encompass any amino acid sequence and include modified sequences (e.g., glycosylated, PEGylated, containing conservative amino acid substitutions, etc.). The term includes naturally occurring (e.g., non-recombinant) proteins. polypeptides, peptides, (particularly those isolated from a *Staphylococcus* bacteria, more particularly from *Staphylococcus aueusr*), and oligopeptides, as well as those which are recombinantly or synthetically synthesized according to methods well known in the art. As used in connection with the present invention the term "protein" is specifically intended to cover naturally occurring proteins which occur in *Staphylococcus* spp.s and useful in treating infection or in generating antibodies useful in treating infection. Where "polypeptide" or "protein" are recited herein to refer to an amino acid sequence of a naturally-occurring protein molecule, "polypeptide," "protein," and like terms are not meant to limit the amino acid sequence to the complete, native amino acid sequence associated with the recited protein molecule. In addition, the polypeptides and proteins of the invention, or fragments thereof, can be generated in synthetic form having D-amino acids rather than the naturally occurring L-amino acids.

"Polynucleotide" as used herein refers to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Where "polynucleotide" is used to refer to a specific polynucleotide sequence (e.g. a RAP protein-encoding polynucleotide), "polynucleotide" is meant to encompass polynucleotides that encode a protein that is functionally equivalent to the recited protein, e.g., polynucleotides that are degenerate variants (i.e., variants in nucleic acid sequence that encode the same amino acid sequence and exist due to the degeneracy of the genetic code), or polynucleotides that encode biologically active variants or fragments of the recited protein.

By "antisense polynucleotide" is meant a polynucleotide having a nucleotide sequence complementary to a given polynucleotide sequence including polynucleotide sequences associated with the transcription or translation of the given polynucleotide sequence (e.g, a promoter) and/or to a coding sequence of the given polynucleotide sequence, where the antisense polynucleotide is capable of hybridizing to a polynucleotide sequence. Of particular interest are antisense polynucleotides capable of inhibiting transcription and/or translation, either in vitro or in vivo.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen et al 1993 Anticancer Drug Des 8:53–63).

The term "antibody" is meant to refer to an immunoglobulin protein which is capable of binding an antigen. Antibody as used herein is meant to include the entire antibody as well as any antibody fragments (e.g., F(ab)', Fab, Fv) capable of binding the epitope, antigen or antigenic fragment of interest. Preferred antibodies for assays and vaccines of the invention are immunoreactive or immunospecific for and therefore specifically and selectively bind to a protein of interest, e.g., an anti-RAP antibody. The term "antibody" encompasses all types of antibodies, e.g., polyclonal, monoclonal, humanized, chimeric, and those produced by the phage display methodology. Particularly preferred antibodies of the invention are antibodies which have a relatively high degree of affinity for RAP. An antibody of the invention is preferably immunoreactive with and immunospecific for a specific species, e.g., RAP obtained from *Staphylococcus aureus*.

"Antigenic fragment" of a protein is meant a portion of such a protein which is capable of binding an antibody.

By "binds specifically" is meant high avidity and/or high affinity binding of an antibody to a specific polypeptide, e.g., epitope of a protein, e.g., RAP protein. Antibody binding to its epitope on this specific polypeptide is preferably stronger than binding of the same antibody to any other epitope, particularly those which may be present in molecules in association with, or in the same sample, as the specific polypeptide of interest, e.g., binds more strongly to epitope fragments of a protein such as RAP so that by adjusting binding conditions the antibody binds almost exclusively to an epitope site or fragments of a desired protein.

By "detectably labeled antibody" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels known in the art include radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds. (Antibodies: A Laboratory Manual (1988) Cold Spring Harbor Laboratory Press, Cold Spring Harbor, N.Y.)).

The instant invention provides polypeptides for the prevention and treatment of *S. aureus* infections. These polypeptides comprise the general formula Y(K or S)PXTNF (SEQ ID NOS: 1 and 2), where X is C, W, or I, preferably W. In a further embodiment, the polypeptides may have the general formula IKKY(K or S) PXTNF (SEQ ID NOS:3 and 4), where X is C, W, or I, preferably W. The polypeptides are preferably at least 10 amino acids in length, more preferably at least seven amino acids in length.

Nucleic acids encoding the polypeptides of the invention are also included in the scope of the invention. Such nucleic acids may be DNA, RNA, or antisense nucleic acids. In an embodiment an isolated DNA molecule of the invention comprises the sequence TAT TCG CCG TGG ACC AAT TTT (SEQ IDNO:5). The nucleic acid molecules of the invention may be provided as synthetic or purified, isolated molecules, including but not limited to "naked DNA"; in vectors such as but not limited to plasmids or viruses, including expression vectors, or complexed to other compounds for administration. Such techniques are well known in the art The polypeptides of the invention are preferably synthesized de novo by any technique commonly known in the art or may be encode;; by nucleic acid, such as RNA or DNA, delivered to the host. Purification from cultures of *S. aureus* bacteria is discussed in the Experimental section below.

The polypeptides of the invention are typically administered to hosts having or at risk of having a staphylococcal infection such as an *S. aureus* infection. The hosts are typically human patients. Animals may also be treated with the compositions of the invention, including but not limited to animals of commercial or veterinary importance such as cows, sheep, and pigs, and experimental animals such as rats, mice, or guinea pigs.

Typically, the compositions of the invention are administered on a daily basis for at least a period of 1–5 days. As used herein, "therapeutic dose" is a dose which prevents, alleviates, abates, or otherwise reduces the severity of symptoms in a patient The compositions of the invention may be used prophylactically to prevent staphylococcal infections or may be therapeutically used after the onset of symptoms. In some embodiments, induction of the formation of antibodies to the administered compound is desirable. In such instances, standard immunization protocols used in the art are preferred. The compositions administered for immunization may optionally include adjuvants.

In some embodiments of the invention, antagonists of the RAP receptor are provided. Without being limited to any one theory, RIP may function by competing with RAP for binding to the RAP receptor, thus acting as an antagonist of the RAP receptor. Such antagonists include but are not limited to antibodies which specifically bind to RAP; antibodies which specifically bind to a RAP ligand; ligands for RAP or RIP; antisense nucleic acids; and peptide, nonpeptide, and peptidomimetic analogs of RAP, RIP, and their ligands.

Antibodies can be synthetic, monoclonal, or polyclonal and can be made by techniques well known in the art. For therapeutic applications, "human" monoclonal antibodies having human constant and variable regions are often preferred so as to minimize the immune response of a patient against the antibody. Such antibodies can be generated by immunizing transgenic animals which contain human immunoglobulin genes. See Jakobovits et al. *Ann NY Acad Sci* 764:525–535 (1995). In connection with synthetic and semi-synthetic antibodies, such terms are intended to cover but are not limited to antibody fragments, isotype switched antibodies, humanized antibodies (e.g., mouse-human, human-mouse, and the like), hybrids, antibodies having plural specificities, fully synthetic antibody-like molecules, and the like.

As discussed below, antibodies can be screened for the ability to block the binding of a ligand to RAP or RIP and/or for other properties, such as the ability to protect in vivo against *S. aureus* infection.

In some embodiments of the invention, antisense nucleic acid molecules are used as antagonists of RAP. Antisense nucleic acid molecules are complementary oligonucleotide strands of nucleic acids designed to bind to a specific sequence of nucleotides to inhibit production of a targeted protein. These agents may be used alone or in combination with other antagonists.

The antisense antagonist may be provided as an antisense oligonucleotide such as RNA (see, for example, Murayama et al. *Antisense Nucleic Acid Drug Dev.* 7:109–114 (1997)). Antisense sequences may also be provided in a viral vector, such as, for example, in hepatitis B virus (see, for example, Ji et al., *J. Viral Hepat.* 4:167–173 (1997)); in adeno-associated virus (see, for example, xiao et al. *Brain Res.* 756:76–83 (1997)); or in other systems including but not limited to an HVJ(Sendai virus)-liposome gene delivery system (see, for example, Kaneda et al *Ann. N.Y. Acad. Sci.* 811:299–308 (1997)); a "peptide vector" (see, for example, Vidal et al. *CR Acad. Sci III* 32):279–287 (1997)); as a gene in an episomal or plasmid vector (see, for example, Cooper et al. *Proc. Natl. Acad. Sci. U.S.A.* 94:6450–6455 (1997), Yew etal. *Hum Gene Ther.* 8:575–584 (1997)); as a gene in a peptide-DNA aggregate (see, for example, Niidome et al., *J. Biol. Chem.* 272:15307–15312 (1997)); as "naked DNA" (see, for example, U.S. Pat. No. 5,580,859 and U.S. Pat. No. 5,589,466); and inlipidic vector systems (see, for example, Lee et al. *Crit Rev Ther Drug Carrier Syst.* 14:173–206 (1997)).

Candidate antagonists of the RAP receptor can be screened for function by a variety of techniques known in the art and/or disclosed within the instant application, such as protection against *S. aureus* infection in a mouse model. A multitude of appropriate formulations of the antagonists of the invention can be found in the formulary known to all pharmaceutical chemists: Remington's *Pharmaceutical Sciences*, (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

The quantities of active ingredient necessary for effective therapy will depend on many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of the active ingredients. Animal testing of effective doses for treatment of particular disorders will provide further predictive indication of human dosage. Various considerations are described, for example, in Goodman and Oilman's *The Pharmacological Basis of Therapeutics*, 7th Edition (1985), MacMillan Publishing Company, New York, and Remington's *Pharmaceutical Sciences* 18th Edition, (1990) Mack Publishing Co, Easton Perm. Methods for administration are discussed therein, including oral, intravenous, intraperitoneal, intramuscular, transdermal, nasal, iontophoretic administration, and the like.

The compositions of the invention may be administered in a variety of unit dosage forms depending on the method of administration. For example, unit dosage forms suitable for oral administration include solid dosage forms such as powder, tablets, pills, and capsules, and liquid dosage forms, such as elixirs, syrups, and suspensions. The active ingredients may also be administered parenterally in sterile liquid dosage forms. Gelatin capsules contain the active ingredient and as inactive ingredients powdered carriers, such as glucose, lactose, sucrose, mannitol, starch, cellulose or cellulose derivatives, magnesium stearate, stearic acid, sodium saccharin, talcum, magnesium carbonate and the like.

Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The compositions of the invention may also be administered via liposomes. Liposomes include emulsions, foams, micelles, insoluble monolayers, liquid crystals, phospholipid dispersions, lamellar layers and the like. In these preparations the composition of the invention to be delivered is incorporated as part of a liposome, alone or in conjunction with a molecule which binds to a desired target, such as antibody, or with other therapeutic or immunogenic compositions. Thus, liposomes either filled or decorated with a desired composition of the invention of the invention can delivered systemically, or can be directed to a tissue of interest where the liposomes then deliver the selected therapeutic/immunogenic polypeptide compositions.

Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. *Ann. Rev. Biophys. Bioeng* 9:467 (1980), U.S. Pat. Nos. 4,235,871, 4,501,728, 4,837, 028, and 5,019,369, incorporated herein by reference.

A liposome suspension containing a composition of the invention may be administered intravenously, locally, topically, etc. in a dose which varies according to, inter alia the manner of administration, the composition of the invention being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more compositions of the invention of the invention, and more preferably at a concentration of 25%–75%.

For aerosol administration, the compositions of the invention are preferably supplied in finely divided form along with a surfactant and propellant. Typical percentages of compositions of the invention are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides maybe employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

The constructs of the invention can additionally be delivered in a depot-type system, an encapsulated form, or an implant by techniques well-known in the art. Similarly, the constructs can be delivered via a pump to a tissue of interest.

Any of the foregoing formulations may be appropriate in treatments and therapies in accordance with the present invention, provided that the active agent in the formulation is not inactivated by the formulation and the formulation is physiologically compatible. Polyclonal and/or monoclonal antibodies to the polypeptides of the present invention may be prepared. The polypeptides of the invention thereof may be prepared as described herein, and coupled to a carrier molecule, for example keyhole limpet hemocyanin, and injected into rabbits at selected times over several months. The rabbit sera may be tested for immunoreactivity to the polypeptides thereof. Monoclonal antibodies may be made by injecting mice with the polypeptides. Monoclonal antibodies may be screened by methods known in the art, as are described, for example, in Harlow and Lane (1988) *Antibodies: A laboratory manual.* Cold Spring Harbor Press, New York, and Goding (1986) *Monoclonal antibodies: Principles and Practice* (2d ed.) Academic Press, New York. The antibodies will be tested for specific immunoreactivity with an epitope of the polypeptides. These antibodies will find use in diagnostic assays or as an active ingredient in a pharmaceutical composition.

For production of polyclonal antibodies, an appropriate target immune system is selected, typically a mouse or rabbit, although other species such as goats, sheep, cows, guinea pigs, and rats maybe used. The substantially purified antigen is presented to the immune system according to methods known in the art The immunological response is typically assayed by an immunoassay. Suitable examples include ELISA, RIA, fluorescent assay, or the like. These antibodies will find use in diagnostic assays or as an active ingredient in a pharmaceutical composition.

Rap Nucleic Acid and Proteins

The present invention also provides a protein (RAP) isolated and purified from a non-pathogenic *Staphylococcus* spp. The RAP protein has a molecular weight of about 38 kDa. In one embodiment, RAP is the protein encoded by a polynucleotide comprising the sequence of SEQ ID NO:12, and comprising an amino acid sequence of SEQ ID NO:13. These sequences are provided in the Sequence Listing below.

RAP Nucleic Acid

The term "RAP gene" is used generically to designate RAP genes and their alternate forms. "RAP gene" is also intended to mean the open reading frame encoding specific RAP proteins, and adjacent 5' and 3' non-coding nucleotide sequences involved in the regulation of expression (e.g., promoter region). The gene may be introduced into an appropriate vector for extrachromosomal maintenance or for integration into the host. In one embodiment the RAP gene comprises the sequence of SEQ ID NO:12.

RAP regulatory sequences may be used to identify cis acting sequences required for transcriptional or translational regulation of RAP expression, especially at different stages of growth (e.g., early, mid, and late log phase), and to identify cis acting sequences and trans acting factors that regulate or mediate RAP expression. Such transcriptional or translational control regions may be operably linked to a RAP coding sequence or other coding sequence.

The nucleic acid compositions used in the subject invention may encode all or a part of the RAP protein as appropriate. Fragments may be obtained of the DNA sequence by chemically synthesizing oligonucleotides in accordance with conventional methods, by restriction enzyme digestion, by PCR amplification, etc. For the most part, DNA fragments will be of at least about ten contiguous nucleotides, usually at least about 15 nt, more usually at least about 18 nt to about 20 nt, more usually at least about 25 nt to about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used.

The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The RAP gene and RAP coding sequence are isolated and obtained in substantial purity, generally as other than an intact bacterial chromosome. Usually, the DNA will be obtained substantially free of other nucleic acid sequences that do not include a RAP sequence or fragment thereof, generally being at least about 50%, usually at least about 90% pure and are typically "recombinant", i.e. flanked by one or more nucleotides with which it is not normally associated on a naturally occurring chromosome.

The DNA sequences are used in a variety of ways. They may be used as probes for identifying RAP coding sequences of other strains of *Staphylococcus* or of other bacteria. Homologs isolated from other stains, species, or genera generally have substantial sequence similarity to one another, i.e. at least 75%, usually at least 90%, more usually at least 95% sequence identity. In general, RAP-encoding sequences of the invention (including homologs, variants, etc.) are characterized by having a sequence identity greater than at least about 65%, preferably at least about 75%, more preferably at least about 85%, and can be greater than at least about 90% or more as determined by the Smith-Waterman homology search algorithm as implemented in MPSRCH program (Oxford Molecular). For the purposes of this invention, a sequence identity is calculated using the Smith-Waterman algorithm as follows: Global DNA sequence identity must be greater than 65% as determined by the Smith-Waterman homology search algorithm as implemented in MPSRCH program (Oxford Molecular) using an affine gap search with the following search parameters: gap open penalty, 12; and gap extension penalty, 1.

Nucleic acids having sequence similarity can also be detected by hybridization under low stringency conditions, for example, at 50° C. and 6×SSC (0.9 M saline/0.09 M sodium citrate) and remain bound when subjected to washing at 55° C. in 1×SSC (0.15 M sodium chloride/0.015 M sodium citrate). In addition, sequence identity may also be determined by hybridization under high stringency conditions, for example, at 50° C. or higher and 0.1×SSC (15 mM saline/0.15 mM sodium citrate). By using probes, particularly labeled probes of DNA sequences, one can isolate homologous or related genes. It may also be possible to identify homologs of RAP from mammalian sources.

The RAP-encoding DNA may also be used to detect expression of the gene in a biological specimen. Methods and materials for probing a sample for the presence of particular nucleotide sequences are well established in the literature and do not require elaboration here. mRNA is isolated from a cell sample. mRNA may be amplified by RT-PCR, using reverse transcriptase to form a complementary DNA strand, followed by polymerase chain reaction amplification using primers specific for the subject DNA sequences. Alternatively, mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to an RAP sequence is indicative of RAP gene expression in the sample.

The RAP nucleic acid sequence may be modified for a number of purposes, particularly where they will be used intracellularly, for example, by being joined to a nucleic acid cleaving agent, e.g. a chelated metal ion, such as iron or chromium for cleavage of the gene; or the like.

The RAP coding sequence and/or promoter sequence may be mutated in various ways known in the art to generate targeted changes in promoter strength, sequence of the encoded protein, etc. The DNA sequence or product of such a mutation will be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain. Other modifications of interest include production of fusion proteins (e.g., with green fluorescent proteins (GFP), luciferase, and the like).

Techniques for in vitro mutagenesis of cloned genes are known. Examples of protocols for scanning mutations may be found in Gustin et al., 1993 Biotechniques 14:22; Barany, 1985 Gene 37:111–23; Colicelli et al., 1985 Mol Gen Genet 199:537–9; and Prentki et al., 1984 Gene 29:303–13. Methods for site specific mutagenesis can be found in Sambrook et al., 1989 Molecular Cloning: A Laboratory Manual, CSH Press, pp. 15.3–15.108; Weiner et al., 1993 Gene 126:35–41; Sayers et al., 1992 Biotechniques 13:592–6; Jones and Winistorfer, 1992 Biotechniques 12:528–30; Barton et al., 1990 Nucleic Acids Res 18:7349–55; Marotti and Tomich, 1989 Gene Anal Tech 6:67–70; and Zhu 1989 Anal Biochem 177:120–4.

RAP Protein

RAP protein can be produced by any suitable means, e.g., by isolated from a bacteria that naturally expresses RAP, by recombinant means (e.g., by expression of a polynucleotide having a sequence of SEQ ID NO:12), by synthetic means, and the like.

In one embodiment, RAP is isolated directly from a strain of Staphylococcus producing RAP, e.g., S. aureus. Typically, wild type cells are collected from postexponential culture broth. Cells are then centrifuged and the supernatant subjected to purification by, for example, filtration followed by lyophilizetion, resuspensionin water, and further purification.

The staphylococci bacterium from which RAP may be isolated may include, but is not necessarily limited to, S. aureus, S. capitus, S. wameri, S. capitis, S. caprae, S. carnosus, S. saprophyticus, S. chronii, S. simulans, S. caseolyticus, S. epidermidis, S. haemolyticus, S. hominis, S. hyicus, S. kloosii, S. lentus, S. lugdunensis, S. scruri, S. simulans, and S. xylosus. Preferably RAP is isolated from S. aureus.

In another embodiment, RAP-encoding nucleic acid is employed to synthesize full-length RAP protein or fragments thereof, particularly fragments corresponding to functional domains (e.g., phosphorylation sites that interact with RAP, etc.); and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The polypeptides may be expressed in prokaryotes or eukaryotes in accordance with conventional ways, depending upon the purpose for expression. For large scale production of the protein, a unicellular organism, such as E. coli, B. subtilis, S. cerevisiae, or cells of a higher organism such as vertebrates, particularly mammals, e.g. COS 7 cells, may be used as the expression host cells. Alternatively, RAP fragments can be synthesized.

With the availability of the polypeptides in large amounts, by employing an expression host, RAP protein can be isolated and purified in accordance with conventional ways, e.g., using HPLC, exclusion chromatography, gel electrophoresis, affinity chromatography, or other purification technique. The purified protein will generally be at least about 80% pure, preferably at least about 90% pure, and may be up to and including 100% pure.

The RAP proteins can be used for the production of antibodies, where short fragments provide for antibodies specific for the particular polypeptide, and larger fragments or the entire protein allow for the production of antibodies over the surface of the polypeptide. Antibodies may be raised to the wild-type or variant forms of RAP. Antibodies may be raised to isolated peptides corresponding to these domains, or to the native protein, e.g. by immunization with cells expressing RAP, immunization with liposomes having RAP protein inserted in the membrane, etc.

Anti-RAP Antibodies

The present invention also provides an antibody that specifically binds and is immunoreactive with RAP. The antibody may be monoclonal, polyclonal or humanized, and is prepared using methods well known in the art. In general, antibodies are prepared in accordance with conventional ways, where the protein or an antigenic portion thereof is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. In a preferred embodiment, the spleen or lymph node cells and myeloma cells are mixed in about 20:1 to about 1:1 ratio, but preferably in about 2:1 ratio. It is preferred that the same species of animal serve as the source of somatic and myeloma cells used in the fusion procedure, where the animal is chosen from rat, mouse, rabbit, cow, chicken, turkey, or man. The fusion of the somatic and myeloma cells produces a hybridoma, which is grown in culture to produce the desired monoclonal antibody by standard procedures. For further description, see, for example, *Monoclonal Antibodies: A Laboratory Manual,* Harlow and Lane eds., Cold Spring Harbor Laboratories, Cold Spring Harbor, New York, 1988. If desired, the mRNA encoding the heavy and light chains may be isolated and mutagenized by cloning in *E. coli,* and the heavy and light chains mixed to further enhance the affinity of the antibody. Alternatives to in vivo immunization as a method of raising antibodies include binding to phage "display" libraries, usually in conjunction with in vitro affinity maturation.

The polyclonal antibodies of the present invention may be produced by injecting a rat, a mouse, a rabbit, a cow, a chicken, or a turkey with RAP to initiate an immunogenic response. RAP may be coupled to a protein carrier such as deyhole limpet hemocyanin (KLH) or bovine serum albumin (BSA). An adjuvant may also be used. After a suitable amount of time to establish a high-titer of anti-RAP antibodies, the serum or eggs are collected. The presence of antibody in the serum or eggs may be tested by radioimmunoassay (RIA), by enzyme-linked immunosorbent assay (ELISA), or by immunoprecipitation. The immunoglobulins may be isolated by the sequential precipitation methods, by conventional methods of "salting out" the protein fractions from a salt solution, or by chromatographical methods well known to those skilled in the art.

Identifying Agents Suitable for Treating *Staphylococcus* Infection

Of particular interest in the present invention is the identification of agents that have activity in affecting the expression and/or function of RAP. In general agents of interest are those that inhibit RAP activity, e.g., by inhibiting the ability of RAP to effect activation of rnaiii. Such agents are candidates for development of treatments for infection of pathogenic *Staphylococcus.* Of particular interest are screening assays for agents that have a low toxicity for human cells and/or high specificity for *Staphylococcus,* preferably with substantially no or little pressure for selection of strains resistant to the action of the agent, and without substantially affecting normal flora of the host (e.g., as distinguished from wide-spectrum antibiotics).

The term "agent" as used herein describes any molecule, e.g. protein or pharmaceutical, with the capability of altering RAP activity, or mimicking or enhancing RIP activity, as described above. Generally a plurality of assay mixtures are run in parallel with different agent concentrations to detect differential responses to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, pheromones, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial (e.g., non-pathogenic *Staphylococcus*), fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Screening of Candidate Agents

A wide variety of in vitro assays may be used to screen candidate agents, including labeled in vitro binding assays, e.g., protein-protein binding, protein-DNA binding assays, electrophoretic mobility shift assays, immunoassays for protein binding, and the like. Purified naturally-occurring or recombinant RAP and RIP proteins, and/or synthetically produced peptides or fragments of RAP and/or RIP, can be used in various screening assays to identify ligands or substrates that bind to, modulate (e.g., increase or inhibit), or mimic the action of the native proteins. The purified proteins may also be used for determination of three-dimensional crystal structure, which can be used for modeling intermolecular interactions, transcriptional regulation, etc.

The screening assay can be a binding assay, wherein one or more of the molecules may be joined to a label, and the label directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures. In general, the particular type of screening assay employed will preferably one amenable to parallel, simultaneous screening of a large number of candidate agents.

Screening assays of the present invention encompass assays that examine the effect of candidate agents on the roles of RAP, and RIP in RNAIII production and/or virulence factor production. For example, the candidate agent may be contacted with pathogenic *Staphylococcus* and the levels of rnaiii transcription in the presence of the agent compared to rnaiii transcription levels in the presence of RIP, RAP, and/or a combination of RIP and RAP. Such screening assays can utilize recombinant host cells containing reporter gene systems such as CAT (chloramphenicol acetyltransferase), β-galactosidase, and the like operably associated with rnaiii or virulence factor genes to facilitate detection of rnaiii or virulence gene transcription or to facilitate detection of RNAIII or virulence factor production. Alternatively, the screening assay can detect rnaiii or virulence factor transcription using hybridization techniques (e.g., Northern blot, PCR, etc.) well known in the art.

A variety of other reagents may be included in the screening assays described herein. Where the assay is a binding assay, these include reagents like salts, neutral proteins, e.g. albumin, detergents, etc. that are used to facilitate optimal protein-protein binding, protein-DNA binding, and/or reduce non-specific or background interactions. Reagents that improve the efficiency of the assay, such as protease inhibitors, nuclease inhibitors, antimicrobial agents, etc. may be used. The mixture of components are added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hours will be sufficient.

Screening of Candidate Agents in an Animal Model

Agents having a desired activity as determined in the assays described above can be further screened for their ability to affect *Staphylococcus* virulence factor production, and to affect *Staphylococcus* infection, in a non-human animal model. The animal model selected will vary with a number of factors including, but not limited to, the particular pathogenic strain of *Staphylococcus* against which candidate agents are to be screened, the ultimate host for which the candidate agents are to serve as therapeutics, etc. Animals suitable for use in screening assays include any animal susceptible to infection by the selected *Staphylococcus* species. For example, where the *Staphylococcus* species is *S. aureus*, the animal model can be a rodent model, preferably a mouse model.

In general, the candidate agent is administered to a non-human animal susceptible to *Staphylococcus* infection, where the animal has been previously infected with *Staphylococcus* or receives an infectious does of *Staphylococcus* in conjunction with the candidate agent. Preferably, the animal has no detectable RAP antibodies. The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired affect is to be achieved), topically, orally, or by any other desirable means. Normally, this screen will involve a number of animals receiving varying amounts and concentrations of the candidate agent (from no agent to an amount of agent hat approaches an upper limit of the amount that can be delivered successfully to the animal), and may include delivery of the agent in different formulations. The agents can be administered singly or can be combined in combinations of two or more, especially where administration of a combination of agents may result in a synergistic effect.

The effect of agent administration upon the animal model can be monitored by any suitable method, such as assessing the number and size of *Staphylococcus*-associated lesions, overall health, etc. Where the candidate agent affects *Staphylococcus* infection in a desirable manner (e.g., by reducing infectious load, facilitating lesion regression, etc.), the candidate agent is identified as an agent suitable for use in treatment of *Staphylococcus* infection.

Identified Candidate Agents

The compounds having the desired pharmacological activity may be administered in a physiologically acceptable carrier to a host for treatment of pathogenic *Staphylococcus* infection. The therapeutic agents may be administered in a variety of ways, orally, topically, parenterally e.g. subcutaneously, intraperitoneally, intravascularly, intrapulmonary (inhalation), etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Treating *Staphylococcus* Infection

The invention provides a method for preventing or treating a human or an animal susceptible to infection by a pathogenic *Staphylococcus* (e.g., *S. aureus* in humans) by administering an agent that inhibits RAP activity in facilitating virulence factor production, e.g., by inhibition RAP-mediated activiation of RNAIII and subsequent virulence factor production.

In one embodiment, the host is treated by administration of RIP or with a RAP inhibitor, such as an anti-RAP antibody, or both. In one embodiment the RAP inhibitor is co-administered with other RAP inhibitors and/or co-administered with other inhibitors of *S. aureus* virulence factor production, e.g., co-administered with RIP. In another embodiment a RAP inhibitor, RIP, and a RAP inhibitor (e.g., an anti-RAP antibody) are administered. Such combination therapies (e.g., administration of multiple RAP inhibitory agents; administration of RAP and RIP; and/or administration of RAP inhibitor, RIP, and/or RAP inhibitor) may involve co-administration or sequential administration of the active components. The dosage regimen may be adjusted to provide the optimum therapeutic response. For example, several divided doses may be administered daily or the dose may be proportionally reduced as indicated by the therapeutic situation. The active compounds may be administered in any convenient manner, such as by oral, intravenous, intramuscular, subcutaneous, buccal, transdermal, or inhalation routes.

Formulations composed of RIP, RAP inhibitor, or both are administered at a therapeutically effective dosage, e.g., a dosage sufficient to improve the chance of successful prevention or treatment of infection. Administration of such a formulation can be via any of the accepted modes of administration for agents that serve similar utilities, preferably by systemic administration.

Human dosage levels for treating infections are known and generally include a daily dose from about 0.1 to 500.0 mg/kg of body weight per day, preferably about 6.0 to 200.0 mg/kg, and most preferably about 12.0 to 100.0 mg/kg. Generally, it is sought to obtain a serum concentration of such a formulation approximating or greater than circulating levels needed to reduce or eliminate any infection in less than 10 days. For administration to a 70 kg person, the dosage range would be about 50 mg to 3.5 g per day, preferably about 100 mg to 2 g per day, and most preferably about 200 mg to 1 g per day. The amount of formulation administered will, of course, be dependent on the subject and the severity of the affliction, the manner and schedule of administration and the judgment of the prescribing physician.

In employing formulation for treatment of infections, any pharmaceutically acceptable mode of administration can be used. The formulations can be administered either alone or in combination with other pharmaceutically acceptable excipients, including solid, semi-solid, liquid or aerosol dosage forms, such as, for example, tablets, capsules, powders, liquids, gels, suspensions, suppositories, aerosols or the like. The formulations can also be administered in sustained or controlled release dosage forms (e.g., employing a slow release bioerodable delivery system), including depot injections, osmotic pumps, pills, transdermal and transcutaneous (including electrotransport) patches, and the like, for prolonged administration of a predetermined rate, preferably in unit dosage forms suitable for single administration of precise dosages.

The compositions will typically include a conventional pharmaceutical carrier or excipient and a formulation of the invention. In addition, these compositions may include other active agents, carriers, adjuvants, etc. Generally, depending on the intended mode of administration, the pharmaceutically acceptable composition will contain about 0.1% to 90%, preferably about 0.5% to 50%, by weight of active compound, the remainder being suitable pharmaceutical excipients, carriers, etc. Actual methods of preparing such dosage forms are known, or will be apparent, to those skilled in this art. For example, see *Remington's Pharmaceutical Sciences*, Mack Publishing Company, Easton, Pa., 15th Edition, 1975.

Parental administration is generally characterized by injection, either subcutaneously, intradermally, intramuscularly, or intravenously, preferably subcutaneously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, and the like.

The percentage of active ingredient contained in such parental compositions is highly dependent on the specific nature thereof, as well as the needs of the subject. However, percentages of active ingredient of 0.01% to 10% in solution are employable, and will be higher if the composition is a solid which will be subsequently diluted to the above percentages. Preferably, the composition will comprise 0.2–2% of the active ingredient in solution.

A more recently devised approach for parental administration employs the implantation of a slow-release or sustained-release system, such that a constant level of dosage is maintained. Various matrices (e.g., polymers, hydrophilic gels, and the like) for controlling the sustained release, and for progressively diminishing the rate of release of active agents are known in the art. See U.S. Pat. Nos. 3,845,770 (describing elementary osmotic pumps); U.S. Pat. Nos. 3,995,651, 4,034,756 and 4,111,202 (describing miniature osmotic pumps); U.S. Pat. Nos. 4,320,759 and 4,449,983 (describing multichamber osmotic systems referred to as push-pull and push-melt osmotic pumps); and U.S. Pat. No. 5,023,088 (describing osmotic pumps patterned for the sequentially timed dispensing of various dosage units).

Formulations of active components may also be administered to the respiratory tract as a nasal or pulmonary inhalation aerosol or solution for a nebulizer, or as a microfine powder for inhalation, alone or in combination with an inert carrier such as lactose, or with other pharmaceutically acceptable excipients. In such a case, the particles of the formulation may advantageously have diameters of less than 50 microns, preferably less than 10 microns. See, e.g., U.S. Pat. No. 5,364,838, which discloses a method of administration for insulin that can be adapted for the administration of formulations of the present invention.

Vaccination

The invention provides a vaccine for inoculating a human or a animal susceptible to infection by a pathogenic *Staphylococcus* (e.g., *S. aureus*) by administering RAP, or an antigenically effective portion of RAP, in a pharmaceutically acceptable carrier, which may optionally comprise an adjuvant. Formulations appropriate for elicitation of the immune response are well known in the art. In general, the host is exposed to the antigen, such as RAP, which perturbs the host's immune system and results in an immune response towards the antigen. An adjuvant can be added with the antigen to increase the immune response to the antigen. The amount of polypeptide administered is an amount sufficient to elicit a protective immune response in the host. Methods for determining such appropriate amounts are routine and well known in the art. For example, RAP and/or antigenically effective portion(s) thereof can be used to vaccinate an animal model of *Staphylococcus* infection. The amounts effective in such animal models can be extrapolated to other hosts (e.g., livestock, humans, etc.) in order to provide for an amount effective for vaccination.

Coated Devices

The invention provides for a device, the surface of which is coated with a composition having an amount of a RAP inhibitory agent (e.g., an anti-RAP antibody or RIP peptides) effective to inhibit production of virulence factors by pathogenic *Staphylococcus*. The coated device may be any device which may be associated with a risk of *Staphylococcus* infection or exposure of a host (e.g., surgery patient, menstruating female, etc.) to *Staphylococcus* virulence factors.

Coated devices encompassed by the present invention include, but are not limited to, catheters, needles, surgical instruments (e.g., scalpels, sponges, retractors, etc.), bandages and bandage materials (e.g., gauze, dressings, etc.), artificial joints, heart valves, and tampons. Such devices have a tendency to bring Staphylococci into contact with the host, or to attract colonizations by staph bacteria (e.g., tampons). In such situations, the coated devices may prevent or reduce Staphylococcus infection, or prevent or reduce the development of serious symptoms associated with exposure to Staphylococcus virulence factors.

The following examples are intended to illustrate, not limit the scope of this invention

EXAMPLES

I. In Vivo Studies in Mice

A. Purification of RAP

In these experiments RAP was purified from post exponential supernatants of wild-type S. aureus (FIG. 1A) as described by Balaban et al. (Proc. Natl. Acad. Sci. U.S.A. 92, 1619 (1995)). Peak fractions (FIGS. 1B, 1C) contained a protein of about 38 kD (FIG. ID). HPLC-purified RAP was run on SDS PAGE, blotted onto a PVDF membrane, Coomassie stained, and the purified 38-kD protein used for N-terminal sequencing by Edman degradation. The $NH_2$-terminal sequence of RAP was determined to be IKKYK-PITN (SEQ ID NO:6). This sequence showed no significant homology to known proteins. We also purified RAP from post exponential supernatants of an agr-null strain in which the entire agr locus was replaced with the tetM marker (Novick et al. EMBO J. 12:3967 (1993)), which suggests that RAP is independent of agr.

B. Immunization with RAP

To test whether immunization with RAP can inhibit S. aureus infection, we used the murine model of cutaneous infection (Bunce et al., Infect. Immun. 60, 2636 (1992)). In this model, when the wild-type Smith diffuse (SD) strain of S. aureus is injected subcutaneously together with dextran beads (Cytodex), a visible, measurable lesion (cellulitis) is induced after 24 hrs. In contrast, no lesion is induced in animals injected with cytodexbeads alone.

Four-eight week old (20–30 g), outbred, immunocompetent, hairless male mice, strain Crl:SKHl(hrhr)Br were obtained from Charles River, Wilmington, Mass. and used for these experiments. For prophylactic vaccination with RAP (purified from a wild type S. aureus strain) or RAP* (purified from an agr-mull), 10 μg RAP, purified on a gel filtration column as described by Balaban et al. (supra), was injected together with complete Freund's adjuvant (CFA) on first injection and incomplete Freund's adjuvant (1CFA) on second and third injection subcutaneously, into 4 week old male hairless immunocompetent mice on days 0, 7 and 21. Control mice were either injected with the adjuvant alone or not injected at all (untreated). Vaccinated and control mice were challenged on day 31 with $1.24 \times 10^8$ Smith Diffuse S. aureus subcutaneously together with 1 mg cytodex beads (10) to induce a local infection. The size of the lesion was measured daily and presented as area=0.5 {p(length) (width)} (Table 1).

After challenge with S. aureus, 72% (24/33) RAP-vaccinated mice remained free of disease as compared to 30% (3/10) controls immunized with complete Freund's adjuvant (CFA) and 0% of untreated controls. This difference was statistically significant (RAP vs untreated: p<0.0001; RAP vs CFA: p≦0.003 1) using Fisher's exact probability test Fisher's Exact Probability Test was used to compare proportions of mice developing lesions and mice developing anti-RAP antibodies among the experimental groups (RAP-vaccinated, CFA controls, untreated controls). Among animals developing lesions post challenge with S. aureus, the size of the lesions was compared using single factor Analysis of Variance. Post-hoc testing was performed using Fisher's protected least significant difference.

In addition, in mice that developed lesions, the mean lesion size was 50% smaller than that of CFA control mice (177 mm$^2$) and 76% smaller than untreated controls (370 mm$^2$). Animals that died had extensive lesions which spread to over one quarter of their body size. Only 3% (1/33) of RAP-vaccinated animals died as a result of challenge whereas 22% of control animals died (5/22).

Figure 2A:
FIG. 2A is a photograph of an immunoblot of sera of vaccinated and control animals. Postexponential supernatant of wild type S. aureus (Lanes 1,2) or purified RAP (Lane 3) was separated on SDS 12% PAGE, western blotted, and membranes were incubated in the presence of: Lane 1: pre-immune (lane 1a) or post-immune (lane Ib) sera collected from a control CFA-injected animal (diluted 1:20). Lane 2: pre-immune sera (lane 2a, diluted 1:20) or post immune sera (lane 2b diluted 1:1000 and lane 3 diluted 1:20). Approximate molecular weight markers are indicated in kilodaltons.

To determine if antibodies to RAP were generated, sera from vaccinated and control animals were analyzed by immunoblotting (FIG. 2A) and binding activity to wild-type S. aureus post-exponential supernatants that contained RAP. To estimate antibody levels against the injected antigen, a drop of blood (50 μl) was collected from the tip of the tail before vaccination (pre-immune sera) and 7 days after the third vaccination period (post-immune sera, 3 days before bacterial challenge). Anti-RAP antibody titer was determined by western blotting. Sera was added to the blot (containing postexponential supernatants) in increasing dilutions, until no band appeared. The highest dilution which still reacted with RAP was the determined titer. Animals vaccinated with RAP developed antibodies to a 38-kD protein, and could also bind to purified RAP.

Figure 2B:
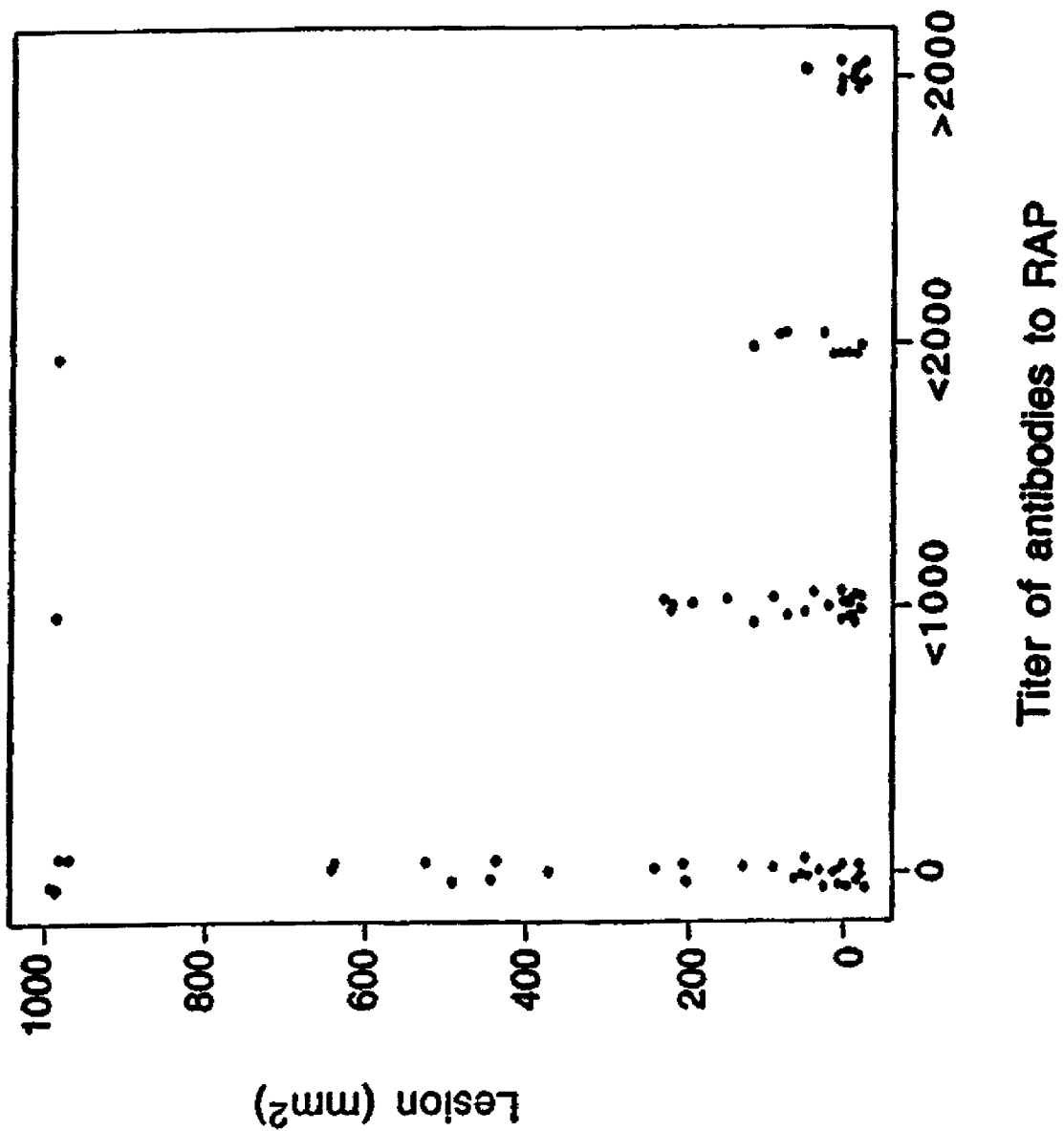
FIG. 2B is a graph depicting the titer of anti-RAP antibodies vs lesion size of vaccinated animals.

Most (33/34) vaccinated animals developed antibodies to RAP (with titers ranging from 1:50–1:16,000) as a result of the injections, whereas control animals did not. However, some of the animals contained pre-immune antibodies to RAP (titers ranging from 1:40–1:2000) and developed smaller lesions upon challenge with S. aureus. The titer of antibodies to RAP (in a total of 81 vaccinated or control animals) inversely correlated with lesion size (FIG. 2B). For purposes of this calculation, animals that died (of extensive cellulitis) were assumed to have a lesion size of 981 mm$^2$.

Mice vaccinated with RAP which purified from a S. aureus agr-null strain as described above had the same degree of protection as animals vaccinated with RAP which was purified from a wild-type strain. This rules out contribution of products from other genes known to regulate RNAIII, such as the octapeptide encoded by agrD (Guangyong et al. Proc. Natl. Acad. Sci. USA. 92, 12055 (1995)).

TABLE 1

Vaccination with RAP as an antigen

| Treatment group | (total n) | no lesion n | (%) | lesion n | mean size (mm$^2$) | death n | (%) |
|---|---|---|---|---|---|---|---|
| RAP | (24) | 17 | (71) | 7 | (96) | 1 | (4) |
| RAP* | (9) | 7 | (78) | 2 | (84) | 0 | (0) |
| CFA | (10) | 3 | (30) | 10 | (177) | 2 | (20) |
| Untreated | (12) | 0 | (0) | 12 | (370) | 3 | (25) |

C. Purification and Amino Acid Sequence of RIP

The non pathogenic coagulase negative staphylococcus presumed to be S. xylosus (ATCC 55619) produces the peptide RIP which inhibits RNAIII transcription (FIG. 3) and competes with RAP for the activation of virulence (Balaban et al, supra). HPLC-purified REP (ibid) was submitted to Edman degradation sequencing. The amino acid sequence was determined to be YSPXTNF (SEQ ID NOS:3 and 4), where X is a modified amino acid, C, I, or W, which has sequence homology to the $NH_2$-terminal sequence of RAP. Without being limited to any one theory, this suggests that gene encoding RIP may be a derivative of the gene encoding RAP.

Figure 3:
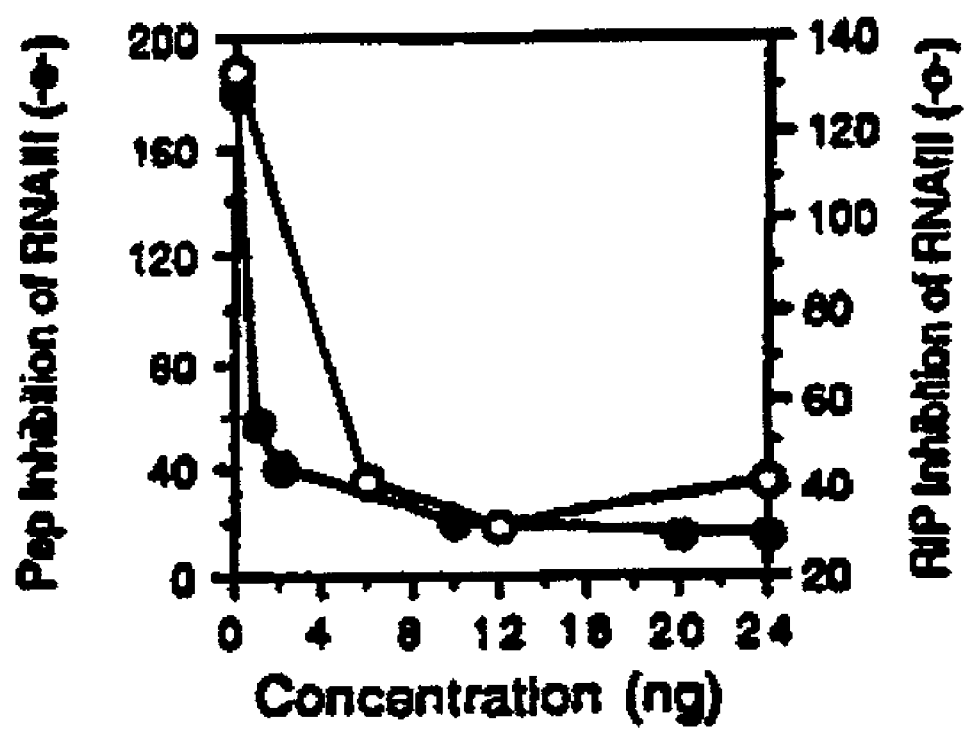
FIG. 3 is a graph depicting the inhibition of RNAIII by purified and synthetic RIP.

A synthetic peptide having the sequence YSPWTNF ((SEQ ID NO:7) denoted Pep herein) was synthesized and tested for its ability to inhibit RNAIII in vitro. The synthetic peptide inhibited induction of RNAIII comparably to RIP (FIG. 3).

D. Suppression of Infection by Purified RAP and RIP

Purified (Balaban etal, *Proc. Natl. Acad. Sci. U.S.A.* 92: 1619 (1995)) and synthetic RIP were tested for their ability to suppress infection in the murine cutaneous *S.aureus* infection model. Smith Diffuse *S. aureus* ($8.5 \times 10^7 - 1.4 \times 10^9$) were incubated in the presence of RIP which was purified from 5 ml postexponential culture broth of ATCC 55619 in saline, or with saline only as a control, with 0.5 mg synthetic RIP (Pep) in a final DMSO (in saline) solution of 3%, or only with 3% DMSO in saline as a control, for 30 min at 37° C. The bacteria+RIP, bacteria+Pep, bacteria+saline or bacteria+DMSO mixture was injected subcutaneously together with cytodex beads (1 mg) into 8 week old male hairless immunocompetent mice to induce a local infection. The size of the lesion was measured daily. For these experiments mice were pre-screened to eliminate individuals with anti-RAP antibodies. A fixed amount of RIP (about 10 mg) attenuated infections caused by increasing inocula of the Smith Diffuse (SD) strain of *S. aureus*.

Of the animals that were injected with $8.5 \times 10^7$ bacteria together with RIP, three of four developed no infection at all, as compared to only one of four control animals that were injected with the bacteria and saline (Table 2). When an increased inoculum of bacteria was used ($1.4 \times 10^5$ cells per injection), four of eight animals were protected, whereas the remaining four developed a lesion that was 55% smaller than that of control animals (Table 2). All (7/7) of the control animals challenged with SD and saline developed a lesion. When a higher number of bacteria was used ($1.4 \times 10^9$), the synthetic RIP (0.5 mg Pep) protected animals, where 90% (9/10) of the animals showed no sign of disease (Table 2).

TABLE 2

Vaccination or suppression of *S. aureus* SD infections

| Treatment | no lesion | | lesion | | death | |
|---|---|---|---|---|---|---|
| | (total n) | n (%) | n | mean size (mm$^2$) | n | (%) |
| RIP Suppression of $8.5 \times 10^7$ SD | | | | | | |
| SD + RIP | (4) | 3 (75) | 1 | (33) | 0 | (0) |
| SD + Saline | (4) | 1 (25) | 3 | (39) | 0 | (0) |
| RIP Suppression of $1.4 \times 10^8$ SD | | | | | | |
| SD + RIP | (8) | 4 (50) | 4 | (45) | 0 | (0) |
| SD + Saline | (6) | 0 (0) | 6 | (100) | 0 | (0) |
| RIP and Pep Suppression of $1.4 \times 10^9$ SD | | | | | | |
| SD + RIP | (10) | 3 (30) | 0 | (0) | 4 | (40) |
| SD + Saline | (10) | 2 (20) | 6 | (160) | 2 | (20) |
| SD + Pep | (10) | 9 (90) | 1 | (56) | 0 | (0) |
| SD + DMSO | (9) | 2 (20) | 4 | (128) | 3 | (22) |

E. Nucleotide Sequence of RIP

Degenerate oligonucleotides were designed from the amino acid sequence YSPWTNF (SEQ ID NO:7). The rip gene was amplified by PCR using Taq DNA polymerase. The PCR product was cloned into pCR2.1 (Invitrogen) and sequenced. The DNA sequence of the tip gene was determined to be TAT TCG CCG TGG ACC AAT TTT (SEQ ID NO:5).

F. Comparison of Synthetic and Natural RIP Peptides

Figure 4A:
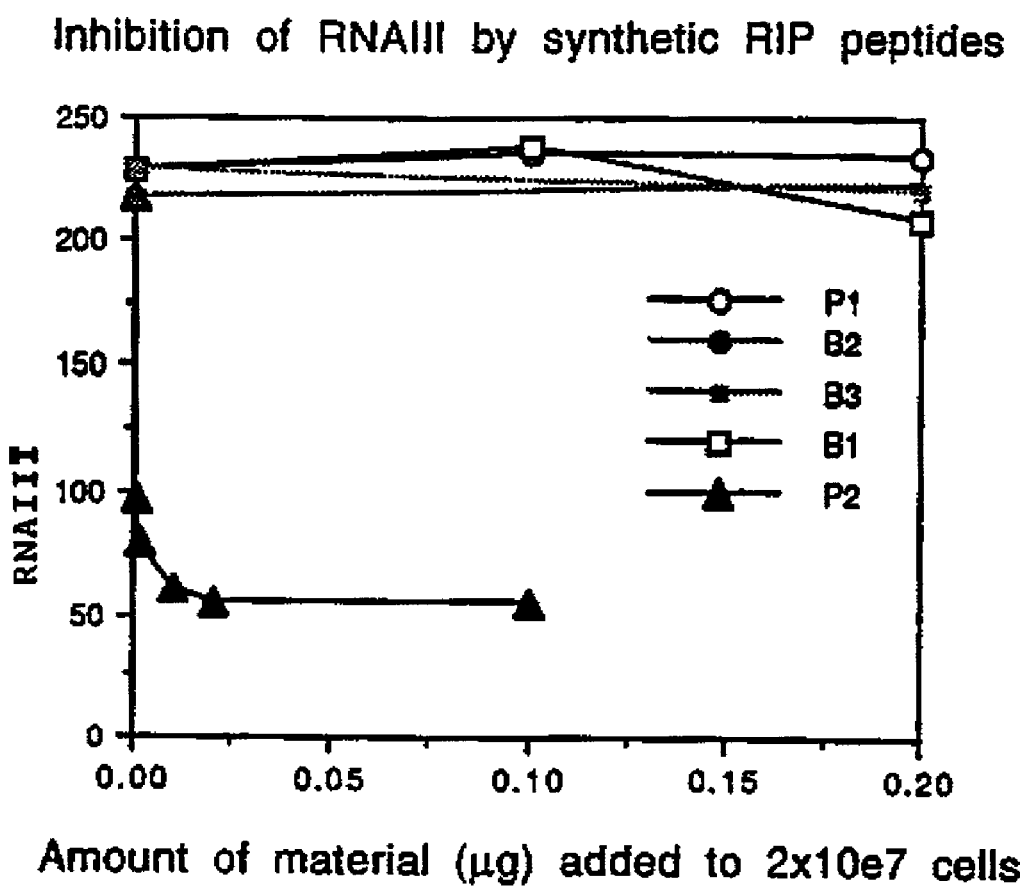
Figure 4C:
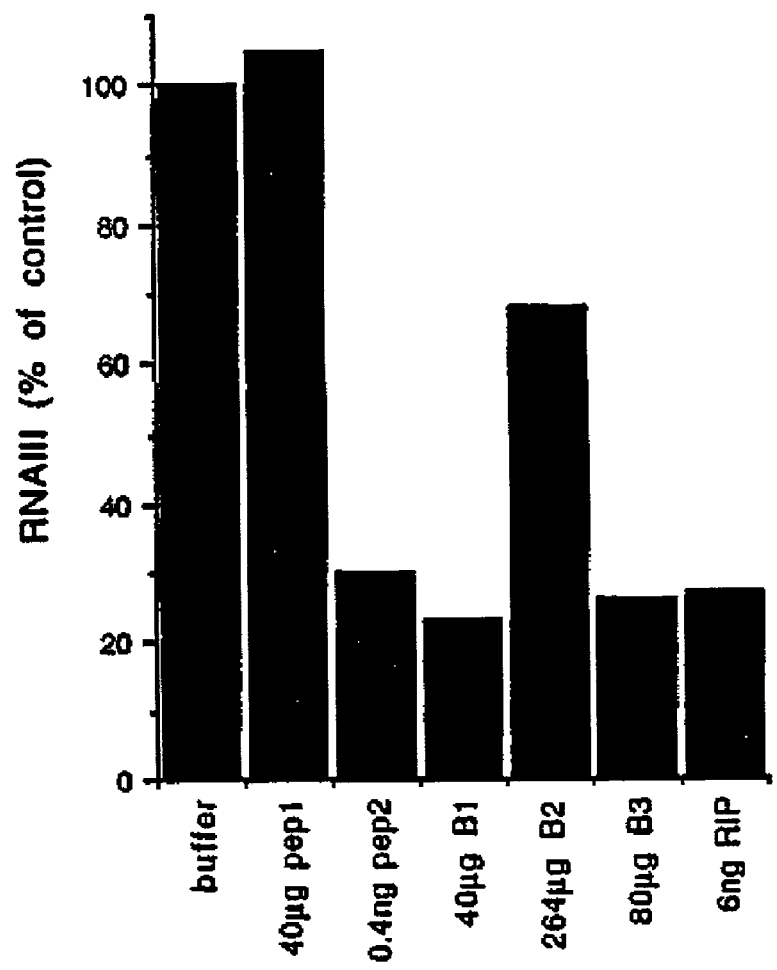
FIG. 4C is a graph depicting competition between RAP and purified or synthetic RIP.

Synthetic peptides corresponding to RIP were synthesized and tested for their ability to inhibit RNAIII in vitro (FIGS. 4A,B) or to compete with RAP on the activation of RNAIII (FIG. 4C). In those Figures RAP includes the sequence IKKYKPITN (SEQ ID NO:6); Pep 1 is PCTNF (SEQ ID NO:8); Pep2 is YSPWTNF (SEQ ID NO:7); B1 is YKPITNF (SEQ ID NO:9); B2 is YSPYINF (SEQ ID NO:10); and B3 is YKPWTNF (SEQ ID NO:11).

In these experiments RIP peptides or control buffer were added to $2 \times 10^7$ ATCC 55620 cells containing the agr P3-blaZ fusion plasmid. Cells were grown in a microtiter plate from early exponential phase of growth (before rnaiii is normally activated) for 2 hr (when rnaiii is normally activated) at 37° C. with shaking. The reaction was stopped by the addition of 10 μl CY containing azide. β-lactamase activity was measured by the addition of 50 μL nitrocefin (132 μg/ml in 0.1 M sodium phosphate buffer, pH 5.8) and read at 490–650 nm. To determine the competition between RAP and purified or synthetic RIP, RAP was added to cells in the presence or absence of RIP and RNAIII was measured 2 hr later. In summary, Pep2 inhibited RNAIII 100% at less than 1 ng. B1 inhibited RNAEI 50% at 2 μg; B2 inhibited RNAIII 50% at 66.6 μg; and B3 inhibited RNAIII 100% at 4 μg.

G. Discussion

Regulatory mechanisms involving autoinducers have been described for other bacterial systems (Rappuoli, etal. in: *Signal Transduction and Bacterial Virulence*, R. Rappuoli, V. Scarlato, B. Arico eds. (Springer Verlag, Heidelberg 1995). pp. 1–4.), including competence and sporulation in *Bacillus subtilis* and in *Streptococcus pneumoniae* (Magnuson et al. *Cell* 77, 207 (1994)), conjugation in *Enterococcus faecalis* (Swift et al., *Trends in Microbiol.* 2, 193 (1994)) and elastase production in *Pseudomonas aeruginosa* (Pearson et al. *Proc. Natl. Acad. Sci. U.S.A.* 92, 1490 (1995)). Furthermore, compounds have been identified which inhibit the phosphorylation of the bacterial two component signal transduction system in *P. aeruginosa* (Roychoudhury, etal., *Proc. Natl. Acad. Sci. U.S.A.* 90, 965 (1993)). Targeting the autoinducers of virulence or the signal transduction they activate may therefore be useful in preventing pathogenesis of other bacteria known to be regulated by global regulons.

Current bacterial vaccines target *S. aureus* or exotoxins it produces ((Lee, *Trends in Microbiol.* 4,162 (1996)), R. Naso and A. Fattom, in: *Novel Strategies in Design and Production of Vaccines*, S. Cohen and A. Shafferman, eds. (Plenum Press, New York, 1996) pp. 133–140), but these approaches met with limited success. With an inexorable increase in antibiotic resistance among bacteria in general (Arthur et al., *Antimicrob. Agents and Chemother.* 37, 1563 (1993)) and among *staphylococci* in particular (Noble et al. *FEMS Microbiol. Lett.* 93, 195 (1992)), there is a need to develop new methods to control bacterial infections. Our approach is to interfere directly with bacterial virulence by interfering with the signal transduction that leads to the production of toxins. By reducing the pathogenic potential of the bacteria, this approach would be synergistic with current anti-microbial therapies and natural host immune mechanisms. Because directed suppression of virulence would not kill the bacteria but rather interfere with its pathogenicity, there would likely be a decrease in selective pressures for the emergence of new resistant *S. aureis* strains.

II. Analysis of Cows for Anti-RAP Antibodies

Serum was collected from lactating dairy cows with one or more positive milk cultures for *S. aureus* (positive) and from lactating cows that have no record of having clinical case of *S. aureus* mastitis through one lactation (negative) (Table 3 A) and from calves which are 1 month and 4 months old (Table 3B). Sera were tested for anti-RAP antibodies by western blotting against post exponential supernatants of wild type *S. aureus*-containing RAP. As shown in Table 3 A, only 10% (2/20) of *S. aureus*-positive cows contain anti-RAP antibodies, while 63% (7/11) of *S. aureus*-negative cows contain anti-RAP antibodies. As shown in Table 3B, 38–46% of the calves contained anti-RAP antibodies. *S. aureus*-negative cows as well as calves will be followed in the future for correlation between titer of anti-RAP antibodies and natural infection rates. As also shown in Table 3 A, 60% (12/20) of the positive cows as compared to 18% (2/11) of the negative cows also contained antibodies to various unidentified proteins in *S. aureus* supernatant (presumed to be antibodies to other *S. aureus* proteins).

Thus, these data indicate that a majority of dairy cows that are negative for *S. aureus* mastitis naturally contain anti-RAP antibodies. These results support the use of RAP as a useful vaccine target site for the prevention of staphylococcal infections.

TABLE 2A

Anti-RAP Antibodies in Cows

| Cow | n | RAP | other *S. aureus* proteins | no anti-*S. aureus* |
|---|---|---|---|---|
| negative | 11 | 7(63%) | 2(18%) | 1(18%) |
| positive | 20 | 2(10%) | 12(60%) | 6(30%) |

TABLE 2B

Anti-RAP Antibodies in Calves

| Calves | n | RAP | other *S. aureus* proteins | no anti-*S. aureus* |
|---|---|---|---|---|
| 1 month old | 20 | 5(38%) | 2(10%) | 13(65%) |
| 4 months old | 20 | 6(46) | 1(5) | 13(65%) |

III. Preparation of Recombinant RAP (Antigen)

A. Purification of RAP and N Terminal Sequencing

RAP is continuously produced by *S. aureus* and can be purified from postexponential culture broth. To purify RAP, wild-type *S. aureus* RN6390B or agr null RN6911 cells were grown to the postexponential phase of growth. Growth culture was centrifuged at 6000×g for 10 min at 4° C. The supernatant was collected and filtered through a 0.22-μm filter to remove residual cells. The supernatant was lyophilized and resuspended in water to 1/10 of the original volume (total 10×).

Fifteen milliliters of total 10× was applied to a 10-kD cutoff membrane (Centriprep 10 (Amicon)). This enabled us to concentrate the material further and to remove material smaller than 10 kDa. One milliliter concentrated material greater than 10 kDa was washed twice in phosphate buffered saline (PBS) by resuspending it each time in 15-ml PBS and reconcentrating it on the Centriprep 10, and the material greater than 10 kDa collected (>10). One hundred microliter material greater than 10 kDa was applied to an HPLC gel filtration column (Bio-Sil SEC-125 300×7.8 mm, Bio-Rad) in 1 mM PBS, pH 7.2 (0.1×PBS), at a flow rate of 0.5 ml/min, and 1-ml fractions collected. Fractions were concentrated to 1/10 of their original volume by lyophilization and tested for activation of RNAIII synthesis as described below.

Active gel filtration fraction (1 ml) was fractionated by anion exchange chromatography (HPLC SynchroPak Q300, Keystone Scientific, Inc.) in water, pH 7.2. The fraction that activated RNAIII synthesis (eluted at 0.75M NaCl) was collected, separated by SDS-PAGE, and western blotted. PVDF membrane was stained by coomassie, and protein band of approximately 38 kDa was amino acid-sequenced commercially by Edman degradation chemistry.

The NH2-terminal sequence of RAP was determined to be IKKYKPITN (SEQ ID NO:6). This sequence was compared to the *S. aureus* database, and the sequence of the open reading frame suggests that it is a possible 279-amino acid polypeptide (FIG. 5) that has a high (76%) sequence identity compared to the *Bacillus subtilis* ribosomal protein L2, and thus is referred to hereafter as rL2.

B. Production of Recombinant RAP (rL2)

To produce rL2, forward and reverse primers corresponding to the 5' and 3' ends of rap gene with added 5' NdeI and 3' BamHI restriction sites were designed based on the sequence of rap (underlined). These primers, 5' GAA TTC CAT <u>ATGGCTATTAAAAAGTATAAG</u> 3' (nucleotides 1–21 (SEQ IDNO:14)) and 5' CGC GCG GAT CC <u>TTATTTTTTCTTACGTCCACG</u> 3' (complement of nucleotides 840–819 (SEQ ID NO: 15)), were used amplify the complete rap gene by PCR, using *S. aureus* chromosomal DNA as a template. Amplified DNA was digested by NdeI and BamHI and ligated into the corresponding sites of pET14b vector (Novagen, Wis.) that possess a six histidine tag at the 5' end of the inserted gene. Plasmid containing rap (pET2-5) was used to transform *E. coli* BL-21(DE3)pLysS (SBpET2-5). Induction of synthesis of recombinant protein was carried out by addition of 1 mM IPTG to the culture and incubation for 3 hours. Cells were harvested and washed once with 50 mM Tris buffer pH 7.9.

Recombinant His-rRAP protein was isolated using a nickel column according to the manufacturer's instructions with some modifications (Xpress Systems Protein Purification, Invitrogen, Calif.). Cell pellet of 50 ml was resuspended in 10 ml binding buffer (20 mM sodium phosphate pH 7.8+0.5M NaCl) and sonicated (for 2 cycles of 15 sec pulses at the maximal level with 30 sec intervals) and then spun in a microcentrifuge.

The supernatant was loaded onto the pre-equilibrated nickel column. Prior to loading, the column containing chelated Sepharose beads was loaded with a charging buffer containing 50 mM $NiCl_2$, and equilibrated with binding buffer. The column was washed three times with five volumes of binding buffer, followed by three washes with five volumes of 20 mM sodium phosphate+0.5M NaCl pH 7.8, then with buffer adjusted to pH 6. Recombinant protein was sequentially eluted from the column using 5ml of the buffer containing 0.5, 1, 2, 3, and 4-M imidazole.

Eluted fractions were extensively dialyzed overnight against TRIS/EDTA buffer (5 mM Tris pH 7.4, 0.5 mM EDTA). Dialyzed fractions were lyophilized, and dried fractions were resuspended in 0.5 ml water, and 30 μl applied on SDS 12.5% PAGE. Gel was western blotted, membrane stained in ponceau to visualize proteins (FIG. 6A), blocked in 1% milk, and incubated with commercially available anti-his antibodies (Boehringer Mannheim) (FIG.

6B). As shown in FIGS. 6A and 6B, highest amounts of pure recombinant protein were eluted by 2M imidazole.

C. Vaccination of Animals with Recombinant RAP (rL2):

4 week old female Balb/C mice (ten mice/group) were injected subcutaneously on days 0, 7, 21 with 50 µg rL2 (50 µg/50 µl PBS) together with 50 µl complete Freund's adjuvant on first injection and incomplete Freund's adjuvant on second and third injections. Control animals were injected with adjuvant/PBS only. Animals were challenged on day 35 with $2 \times 10^9$ Smith Diffuse S. aureus (SD) prepared as described below. Animals were observed daily for mortality, overall health and development of lesion. The size of the lesion was measured (area=0.5 7 (length) (width).

Preparation of bacteria for challenge: Smith Diffuse S. aureus was grown overnight at 37° C. on blood agar plates. Bacteria was suspended in PBS at $2 \times 10^{10}$ cells/ml. $2 \times 10^9$ (100 µl) cells were injected to vaccinated and control animals subcutaneously, together with 1 mg cytodex beads, to induce a local infection.

Antibody level as determined by ELISA. A drop of blood was collected from the tip of the tail before the first vaccination and 10 days after the third vaccination. ELISA plates were coated overnight with 50 µl of 25 µg/ml antigen or with 3% BSA as a control. Wells were then blocked with 3% BSA for 3 hrs at room temperature, and 50 µl sera (diluted 1:1000 in PBS) was applied for 2.5 hrs at room temperature. Unbound antibody was removed and wells were washed 5×2min with PBS with 0.05% Tween 20. 50 µl peroxidase-conjugated anti-mouse antibody (Sigma) diluted 1:2000 with PBS/Tween was applied for 1 hr 37° C. Unbound antibody was removed, and wells were washed as above, and bound antibody was detected by ABTS (Sigma) according to the manufacturer's instructions.

Results of Vaccination Experiments

Development of antibody to the antizen: All vaccinated animals developed an antibody titer (>1000) to the injected antigen. None of the control animals had a detectable antibody level to the injected antigen.

Mortality post challenge: As shown in FIG. 7, of 10 control animals vaccinated with adjuvant only, 3 animals died within the first day post challenge, and another mouse died on the second day. Of 10 animals vaccinated with rL2, none died within the first day, one died on the second day and another died on the third day.

Lesion: All surviving animals developed a lesion and its size was determined on the fifth day post challenge. As shown in FIG. 8, the average lesion size of control animals was 7 cm$^2$, while the average lesion size of animals vaccinated with rL2 was only 2.5 cm$^2$.

Conclusions

Animals vaccinated with rL2 had delayed mortality and a 50% reduction in mortality rate, and a 65% reduction in lesion size. These results suggest that rL2 can confer protection to a S. aureus infection. Of note is the fact that the number of bacteria used for challenge was exceptionally high and it is expected that if a lower number of bacteria were present, protection level from infection could be higher.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

I claim:

1. An isolated RNAIII Activating Protein polypeptide having an amino acid sequence of SEQ ID NO: 13.

2. A vaccine comprising the RNAIII Activating Protein polypeptide of claim 1.

* * * * *

SEQUENCE LISTING

```
<160> NUMBER OF SEQ ID NOS: 15

<210> SEQ ID NO 1
<211> LENGTH: 7
<212> TYPE: PRT
<213> ORGANISM: Artificial Sequence
<220> FEATURE:
<221> NAME/KEY: MOD_RES
<222> LOCATION: (4)
<223> OTHER INFORMATION: Cys, Trp or Ile, preferably Trp
<220> FEATURE:
<223> OTHER INFORMATION: Description of Artificial Sequence: Formula
      peptide sequence

<400> SEQUENCE: 1

Tyr Lys Pro Xaa Thr Asn Phe
  1               5

<210> SEQ ID NO 2
<211> LENGTH: 7
<212> TYPE: PRT
<213> ORGANISM: Artificial Sequence
<220> FEATURE:
<221> NAME/KEY: MOD_RES
<222> LOCATION: (4)
<223> OTHER INFORMATION: Cys, Trp or Ile, preferably Trp
<220> FEATURE:
```

```
<223> OTHER INFORMATION: Description of Artificial Sequence: Formula
      peptide sequence

<400> SEQUENCE: 2

Tyr Ser Pro Xaa Thr Asn Phe
 1               5

<210> SEQ ID NO 3
<211> LENGTH: 10
<212> TYPE: PRT
<213> ORGANISM: Artificial Sequence
<220> FEATURE:
<221> NAME/KEY: MOD_RES
<222> LOCATION: (7)
<223> OTHER INFORMATION: Cys, Trp or Ile, preferably Trp
<220> FEATURE:
<223> OTHER INFORMATION: Description of Artificial Sequence: Formula
      peptide sequence

<400> SEQUENCE: 3

Ile Lys Lys Tyr Lys Pro Xaa Thr Asn Phe
 1               5                  10

<210> SEQ ID NO 4
<211> LENGTH: 10
<212> TYPE: PRT
<213> ORGANISM: Artificial Sequence
<220> FEATURE:
<221> NAME/KEY: MOD_RES
<222> LOCATION: (7)
<223> OTHER INFORMATION: Cys, Trp or Ile, preferably Trp
<220> FEATURE:
<223> OTHER INFORMATION: Description of Artificial Sequence: Formula
      peptide sequence

<400> SEQUENCE: 4

Ile Lys Lys Tyr Ser Pro Xaa Thr Asn Phe
 1               5                  10

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tattcgccgt ggaccaattt t                                              21

<210> SEQ ID NO 6
<211> LENGTH: 9
<212> TYPE: PRT
<213> ORGANISM: Staphylococcus aureus

<400> SEQUENCE: 6

Ile Lys Lys Tyr Lys Pro Ile Thr Asn
 1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7
```

-continued

Tyr Ser Pro Trp Thr Asn Phe
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Cys Thr Asn Phe
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Lys Pro Ile Thr Asn Phe
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Ser Pro Ile Thr Asn Phe
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Lys Pro Trp Thr Asn Phe
1               5

<210> SEQ ID NO 12
<211> LENGTH: 840
<212> TYPE: DNA
<213> ORGANISM: Staphylococcus sp.
<220> FEATURE:
<221> NAME/KEY: CDS
<222> LOCATION: (1)..(837)

<400> SEQUENCE: 12

```
atg gct att aaa aag tat aag cca ata aca aat ggt cgt cgt aat atg      48
Met Ala Ile Lys Lys Tyr Lys Pro Ile Thr Asn Gly Arg Arg Asn Met
1               5                   10                  15 act tcg tta gat ttc gca gaa atc acg aaa act aca cct gaa aag tca      96
Thr Ser Leu Asp Phe Ala Glu Ile Thr Lys Thr Thr Pro Glu Lys Ser
            20                  25                  30 tta tta aaa ccg cta ccg aaa aaa gcg gga cgt aac aac caa ggt aaa     144
```

-continued

```
Leu Leu Lys Pro Leu Pro Lys Lys Ala Gly Arg Asn Asn Gln Gly Lys
         35                  40                  45 ttg act gta aga cac cat ggt ggt gga cac aaa cgt caa tac cgt gtt    192
Leu Thr Val Arg His His Gly Gly Gly His Lys Arg Gln Tyr Arg Val
     50                  55                  60 atc gat ttc aaa cgt aac aaa gat ggt atc aat gca aaa gtt gat tct    240
Ile Asp Phe Lys Arg Asn Lys Asp Gly Ile Asn Ala Lys Val Asp Ser
 65                  70                  75                  80 att caa tat gat cca aac cgc tca gca aac atc gct tta gtt gta tat    288
Ile Gln Tyr Asp Pro Asn Arg Ser Ala Asn Ile Ala Leu Val Val Tyr
                 85                  90                  95 gca gac ggt gaa aaa cga ata tat cat tgc att gct cct aaa gga tta    336
Ala Asp Gly Glu Lys Arg Ile Tyr His Cys Ile Ala Pro Lys Gly Leu
            100                 105                 110 gaa gta ggt caa atc gtt gaa agt ggt gct gaa gct gac act aaa gtt    384
Glu Val Gly Gln Ile Val Glu Ser Gly Ala Glu Ala Asp Thr Lys Val
        115                 120                 125 ggt aac gca tta cca tta caa aac att cca gtt ggt aca gta gta cac    432
Gly Asn Ala Leu Pro Leu Gln Asn Ile Pro Val Gly Thr Val Val His
    130                 135                 140 aac atc gag ctt aaa cct ggt aaa ggt gga caa atc gct cgt tca gct    480
Asn Ile Glu Leu Lys Pro Gly Lys Gly Gly Gln Ile Ala Arg Ser Ala
145                 150                 155                 160 ggt gca agt gct caa gta ctt ggt aaa gaa ggt aaa tac gta tta atc    528
Gly Ala Ser Ala Gln Val Leu Gly Lys Glu Gly Lys Tyr Val Leu Ile
                165                 170                 175 aga tta aga tct ggt gaa gtt cgt atg atc tta tct act tgc cgt gct    576
Arg Leu Arg Ser Gly Glu Val Arg Met Ile Leu Ser Thr Cys Arg Ala
            180                 185                 190 aca atc ggt caa gtt ggt aac cta caa cac gaa tta gtt aac gtt ggt    624
Thr Ile Gly Gln Val Gly Asn Leu Gln His Glu Leu Val Asn Val Gly
        195                 200                 205 aaa gcc gga cgt tca aga tgg aaa ggt atc cgt cca aca gtt cgt ggt    672
Lys Ala Gly Arg Ser Arg Trp Lys Gly Ile Arg Pro Thr Val Arg Gly
    210                 215                 220 tct gta atg aac cct aac gat cac cca cac ggt ggt ggt gaa ggt cgt    720
Ser Val Met Asn Pro Asn Asp His Pro His Gly Gly Gly Glu Gly Arg
225                 230                 235                 240 gct cct atc ggt aga cca tct cca atg tca cca tgg ggt aaa cct acg    768
Ala Pro Ile Gly Arg Pro Ser Pro Met Ser Pro Trp Gly Lys Pro Thr
                245                 250                 255 ctt ggt aag aaa act cgt cgt ggt aaa aaa tca tca gac aaa ctt atc    816
Leu Gly Lys Lys Thr Arg Arg Gly Lys Lys Ser Ser Asp Lys Leu Ile
            260                 265                 270 gtt cgt gga cgt aag aaa aaa taa                                    840
Val Arg Gly Arg Lys Lys Lys
        275
```

<210> SEQ ID NO 13
<211> LENGTH: 279
<212> TYPE: PRT
<213> ORGANISM: Staphylococcus sp.

<400> SEQUENCE: 13

```
Met Ala Ile Lys Lys Tyr Lys Pro Ile Thr Asn Gly Arg Arg Asn Met
 1               5                  10                  15

Thr Ser Leu Asp Phe Ala Glu Ile Thr Lys Thr Thr Pro Glu Lys Ser
             20                  25                  30

Leu Leu Lys Pro Leu Pro Lys Lys Ala Gly Arg Asn Asn Gln Gly Lys
         35                  40                  45
```

```
Leu Thr Val Arg His His Gly Gly His Lys Arg Gln Tyr Arg Val
 50                  55                  60

Ile Asp Phe Lys Arg Asn Lys Asp Gly Ile Asn Ala Lys Val Asp Ser
 65                  70                  75                  80

Ile Gln Tyr Asp Pro Asn Arg Ser Ala Asn Ile Ala Leu Val Val Tyr
             85                  90                  95

Ala Asp Gly Glu Lys Arg Ile Tyr His Cys Ile Ala Pro Lys Gly Leu
            100                 105                 110

Glu Val Gly Gln Ile Val Glu Ser Gly Ala Glu Ala Asp Thr Lys Val
            115                 120                 125

Gly Asn Ala Leu Pro Leu Gln Asn Ile Pro Val Gly Thr Val His
130                 135                 140

Asn Ile Glu Leu Lys Pro Gly Lys Gly Gly Gln Ile Ala Arg Ser Ala
145                 150                 155                 160

Gly Ala Ser Ala Gln Val Leu Gly Lys Glu Gly Lys Tyr Val Leu Ile
            165                 170                 175

Arg Leu Arg Ser Gly Glu Val Arg Met Ile Leu Ser Thr Cys Arg Ala
            180                 185                 190

Thr Ile Gly Gln Val Gly Asn Leu Gln His Glu Leu Val Asn Val Gly
            195                 200                 205

Lys Ala Gly Arg Ser Arg Trp Lys Gly Ile Arg Pro Thr Val Arg Gly
210                 215                 220

Ser Val Met Asn Pro Asn Asp His Pro His Gly Gly Gly Glu Gly Arg
225                 230                 235                 240

Ala Pro Ile Gly Arg Pro Ser Pro Met Ser Pro Trp Gly Lys Pro Thr
            245                 250                 255

Leu Gly Lys Lys Thr Arg Arg Gly Lys Lys Ser Ser Asp Lys Leu Ile
            260                 265                 270

Val Arg Gly Arg Lys Lys Lys
            275

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gaattccata tggctattaa aaagtataag                                    30

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgcgcggatc cttatttttt cttacgtcca cg                                 32
```